US011701052B2

(12) United States Patent
Wood et al.

(10) Patent No.: US 11,701,052 B2
(45) Date of Patent: Jul. 18, 2023

(54) METHODS AND APPARATUS FOR CORTICAL STIMULATION MAPPING DURING SURGICAL PROCEDURES

(71) Applicant: SYNAPTIVE MEDICAL INC., Toronto (CA)

(72) Inventors: Michael Frank Gunter Wood, Toronto (CA); Arun Victor Jagga, Toronto (CA); Murugathas Yuwaraj, Toronto (CA)

(73) Assignee: Synaptive Medical Inc.

( * ) Notice: Subject to any disclaimer, the term of this patent is extended or adjusted under 35 U.S.C. 154(b) by 1031 days.

(21) Appl. No.: 16/428,112

(22) Filed: May 31, 2019

(65) Prior Publication Data
US 2019/0336029 A1  Nov. 7, 2019

Related U.S. Application Data

(63) Continuation of application No. 15/026,300, filed as application No. PCT/IB2015/057668 on Oct. 7, 2015, now abandoned.

(51) Int. Cl.
*A61B 17/34* (2006.01)
*A61B 5/00* (2006.01)
(Continued)

(52) U.S. Cl.
CPC ............ *A61B 5/369* (2021.01); *A61B 5/24* (2021.01); *A61B 5/291* (2021.01); *A61B 5/37* (2021.01); *A61B 5/38* (2021.01); *A61B 5/6865* (2013.01); *A61B 5/6868* (2013.01); *A61B 17/3421* (2013.01); *A61B 17/3423* (2013.01); *A61N 1/0529* (2013.01); *A61N 1/0539* (2013.01); *A61N 1/36017* (2013.01); *A61B 5/064* (2013.01); *A61B 34/25* (2016.02); *A61B 2034/2055* (2016.02); *A61B 2562/04* (2013.01)

(58) Field of Classification Search
CPC ............ A61B 17/3421; A61B 17/3423; A61B 2034/2055; A61B 2562/04; A61B 34/25; A61B 5/064; A61B 5/24; A61B 5/291; A61B 5/369; A61B 5/37; A61B 5/38; A61B 5/6865; A61B 5/6868; A61N 1/0529; A61N 1/0539; A61N 1/36017
See application file for complete search history.

(56) References Cited

U.S. PATENT DOCUMENTS

| 4,406,658 A | 9/1983 | Lattin et al. |
| 5,685,313 A | 11/1997 | Mayevsky |

(Continued)

OTHER PUBLICATIONS

USPTO, Final Rejection, dated May 24, 2018, re U.S. Appl. No. 15/026,300.

(Continued)

*Primary Examiner* — Michael T Rozanski

(57) ABSTRACT

An apparatus and method is provided for intraoperative tissue stimulation during port-based surgery. The apparatus includes an access port and electrical terminals attached to the access port for tissue stimulation. In an alternative embodiment, the apparatus may include an access port, with or without electrical terminals attached to the access port for tissue stimulation, and electrocorticography sensors attached to the access port. The method includes inserting an access port into a tissue, applying an electrical potential to the tissue using electrical terminals attached to the access port, and measuring consequent neural activity using electrocorticography sensors attached to the access port.

18 Claims, 35 Drawing Sheets

(51) Int. Cl.

| | | |
|---|---|---|
| *A61N 1/36* | (2006.01) |
| *A61B 1/05* | (2006.01) |
| *A61B 5/369* | (2021.01) |
| *A61N 1/05* | (2006.01) |
| *A61B 5/24* | (2021.01) |
| *A61B 5/38* | (2021.01) |
| *A61B 5/291* | (2021.01) |
| *A61B 5/37* | (2021.01) |
| *A61B 34/20* | (2016.01) |
| *A61B 5/06* | (2006.01) |
| *A61B 34/00* | (2016.01) |

(56) References Cited

U.S. PATENT DOCUMENTS

| | | | |
|---|---|---|---|
| 6,109,270 A | 8/2000 | Mah et al. | |
| 6,694,162 B2 * | 2/2004 | Hartlep | A61B 5/743 600/378 |
| 8,755,906 B2 | 6/2014 | Moffitt et al. | |
| 2004/0199235 A1 | 10/2004 | Younis | |
| 2005/0177209 A1 | 8/2005 | Leung et al. | |
| 2006/0217705 A1 | 9/2006 | Godara et al. | |
| 2007/0173902 A1 | 7/2007 | Maschino et al. | |
| 2008/0114233 A1 | 5/2008 | McIntyre et al. | |
| 2010/0113959 A1 | 5/2010 | Pascual-Leone et al. | |
| 2011/0288400 A1 | 11/2011 | Russell et al. | |
| 2011/0295350 A1 | 12/2011 | Mercanzini et al. | |
| 2012/0010651 A1 | 1/2012 | Thramann et al. | |
| 2014/0357979 A1 | 12/2014 | Basser | |
| 2015/0011843 A1 | 1/2015 | Toth et al. | |
| 2015/0202432 A1 | 7/2015 | Somogyi et al. | |
| 2016/0110911 A1 | 4/2016 | Frank et al. | |

OTHER PUBLICATIONS

Cao, Ning. Recovering local neural tract directions and reconstructing neural pathways in high angular resolution diffusion MRI. University of Kentucky, 2013.

Non-Final Rejection, dated Jan. 22, 2018, by USPTO, re U.S. Appl. No. 15/026,300.

* cited by examiner

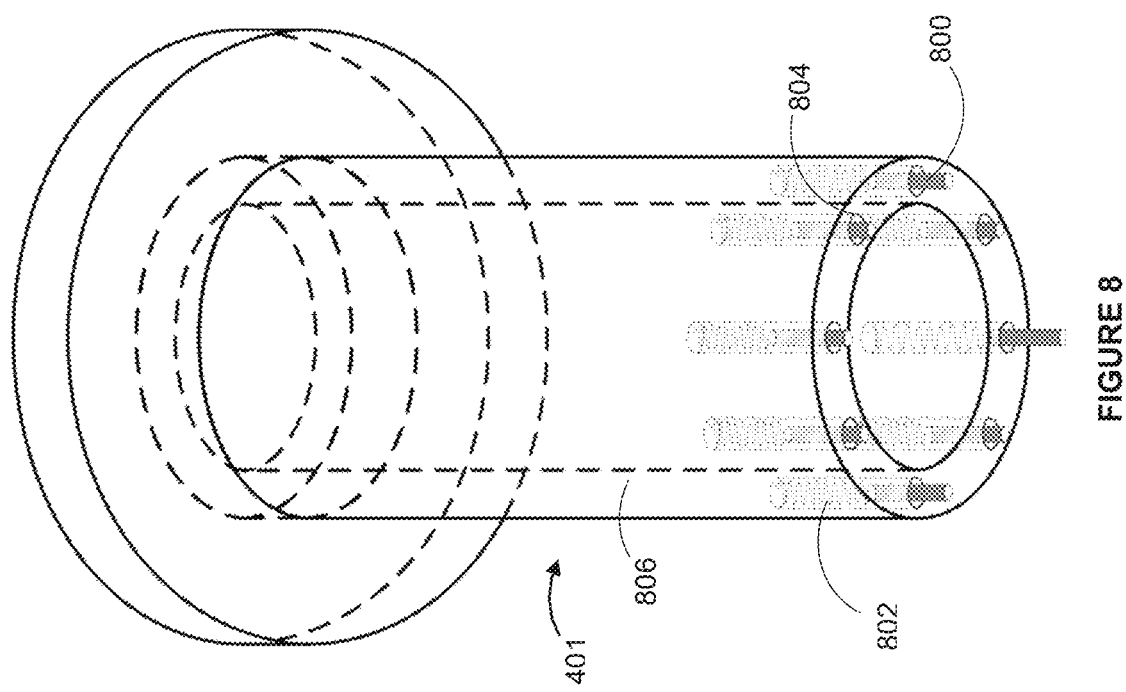

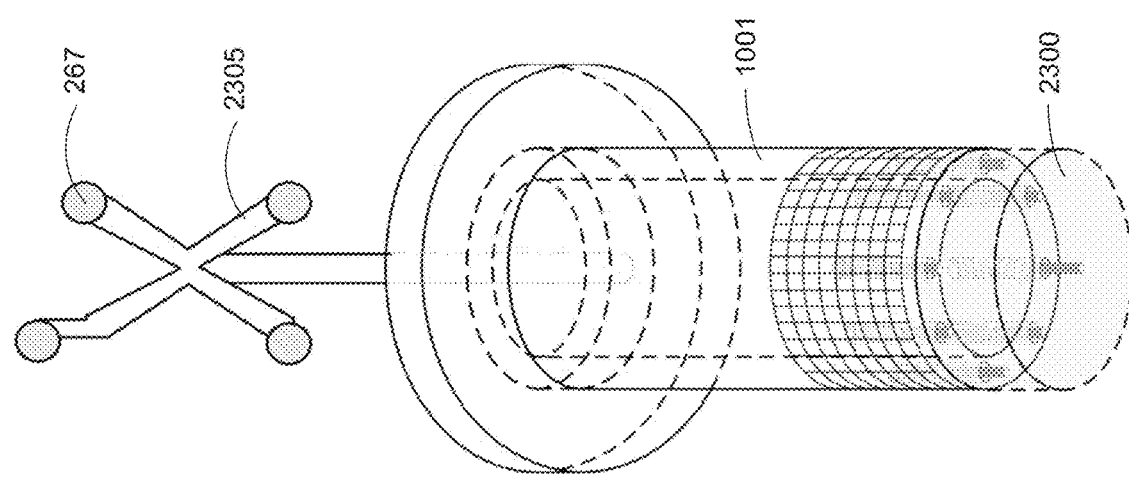

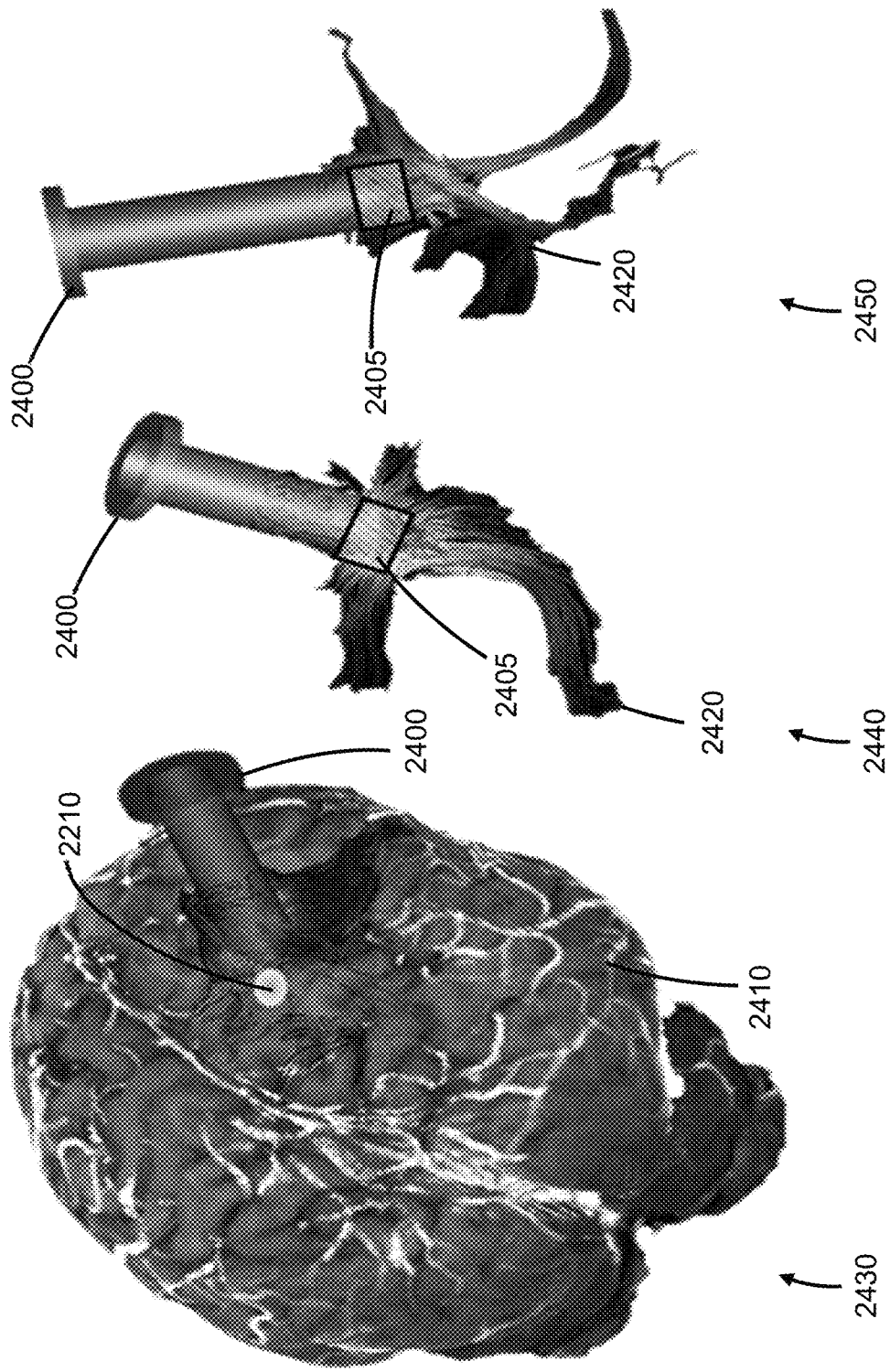

METHODS AND APPARATUS FOR CORTICAL STIMULATION MAPPING DURING SURGICAL PROCEDURES

RELATED APPLICATIONS

This application is a CON of Ser. No. 15/026,300 having a filing date of Mar. 31, 2016, which is a 371 of PCT/IB15/57668.

FIELD

The present disclosure relates to image guided medical procedures using a minimally invasive corridor or access port and more specifically to cortical stimulation.

BACKGROUND

Corridor-based or port-based surgery is a minimally invasive neurosurgical procedure allowing a surgeon to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Minimally invasive brain surgery using access ports is a recently conceived method of performing surgery on brain tumors previously considered inoperable. One object of the present invention is to provide a system and method to assist in minimally invasive brain surgery as well as commonly performed cortical mapping and intracranial procedures. To address intracranial surgical concerns, specific products such as the NICO BrainPath™ port have been developed for port-based surgery.

In presently performed neurosurgical procedures cortical mapping is commonly used to identify important functional areas of the brain to be avoided when performing the operation for example, a tumor resection or Montreal procedure. Cortical mapping may also be used to determine the location in the brain where a stimulus is being applied by the surgeon in order to assist the surgeon in navigating the eloquent areas of the brain. The most commonly applied method of stimulation is performed using a stimulation electrode (bipolar or monopolar as known in the art) to induce a current within a functional region of the brain to induce a response in the patient affecting that function. If a response of that function isn't observed, the voltage applied is increased until a safety threshold voltage is reached, after which it is assumed the area is not the predicted functional area of the brain initially hypothesized. If however a response is detected, than that response, depending on what function it affects can be used by the surgeon to map out the patient's brain for navigational purposes. This is mainly used to less traumatically perform any resection procedure in the patient's brain by avoiding important functional areas such as the motor cortex.

Given the procedure described above, it is apparent that a surgeon may typically have to rely on their own anatomical knowledge of human brain anatomy and experience to effectively employ the information being provided by the cortical mapping exercise in reducing trauma to the patient. This may include remembering which functional areas each placed electrode in the brain corresponded to, and where that area would map to an anatomical atlas of the brain. In addition electrical stimulation of the brain has setbacks such as the occurrence of an epileptic response of the brain following a stimulation event. Other setbacks include a lack of navigation devices customized for this type of procedure and the inability to use stimulation to improve the information available on the patient's brain scan.

SUMMARY

An object of the present invention is to provide methods and devices for conduit based cortical stimulation mapping during port based surgical procedures.

Thus by one broad aspect of the present invention, an apparatus for intraoperative tissue stimulation is provided comprising: an access port having a hollow cylindrical body for receiving tools, a distal end for insertion into a tissue and a proximal end to remain substantially at the surface of the tissue; and one or more electrical terminals attached to the access port for tissue stimulation.

By another broad aspect of the present invention an apparatus for intraoperative tissue stimulation is provided comprising: an access port having a hollow cylindrical body for receiving tools, a distal end for insertion into a tissue and a proximal end to remain substantially at the surface of the tissue; and one or more electrocorticography sensors attached to the access port.

By another broad aspect of the present invention, a method is provided for intraoperative tissue stimulation comprising: inserting an access port into a tissue; and applying an electrical potential to the tissue using one or more electrical terminals attached to the access port.

A better understanding of the functional and advantageous aspects of the disclosure can be realized by reference to the following detailed description and drawings.

BRIEF DESCRIPTION OF THE DRAWINGS

FIG. 8 Illustrates the functional port apparatus with deformable stimulation electrodes.

FIG. 23 Illustrates the stimulation ECoG port apparatus having a defined ROI (regions of interest) and a tracking apparatus.

FIG. 24A, FIG. 24B and FIG. 24C Illustrates the application of the ROI with a virtual stimulation ECoG port apparatus in a neurosurgical planning platform.

DETAILED DESCRIPTION

Figure 1:
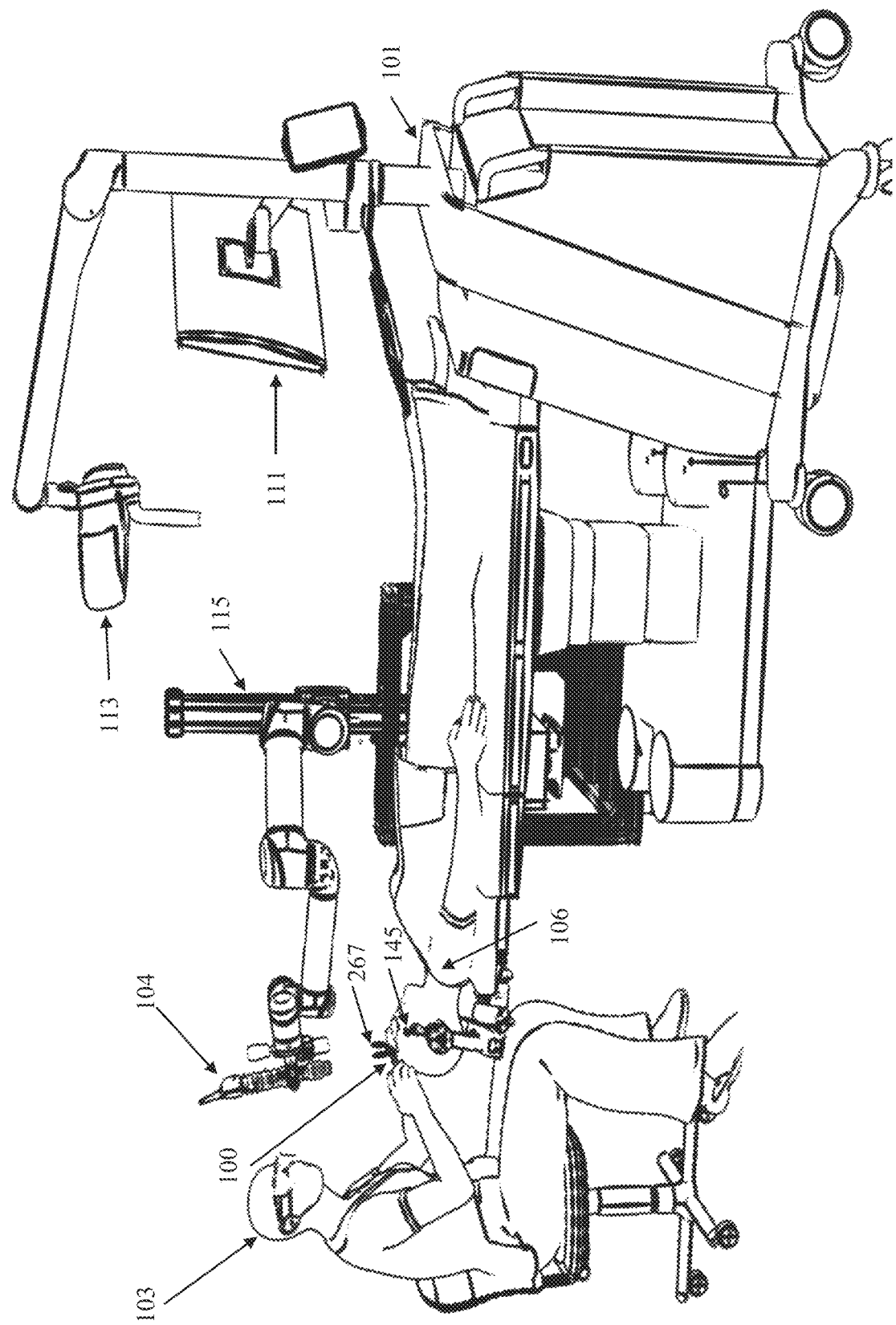
FIG. 1 Illustrates a port based neurosurgical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide stimulation and detection devices that are insertable into a subject or patient for analysis and stimulation of internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

Several embodiments of the present disclosure seek to address the aforementioned inadequacies of existing devices and methods to support surgical procedures utilizing surgical tools.

Figure 2B:
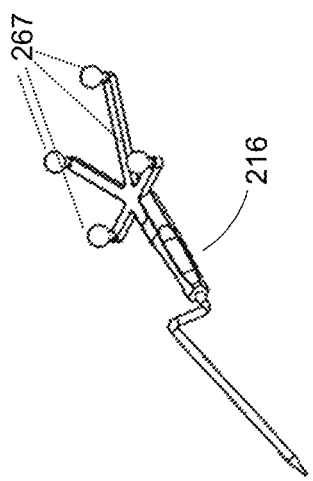
FIG. 2A and FIG. 2B Illustrates commonly used neurosurgical tools.
Figure 2A:
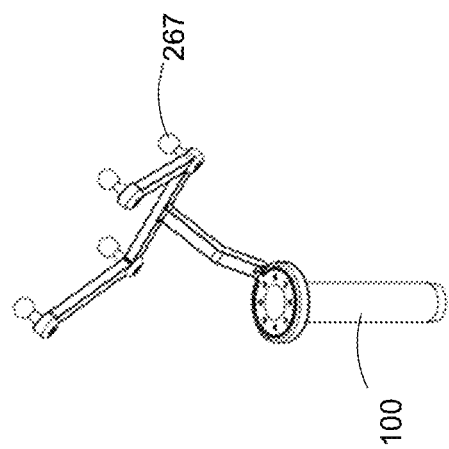

Minimally invasive brain surgery using access ports is a recently conceived method of performing surgery on brain tumors previously considered inoperable. One object of the present invention is to provide a system and method to assist in minimally invasive brain surgery. To address intracranial surgical concerns, specific products such as the NICO Brain-Path™ port have been developed for port-based surgery. As seen in FIG. 1 and FIG. 2A and FIG. 2B, port 100 comprises of a cylindrical assembly formed of an outer sheath. Port 100 may accommodate an introducer which is an internal cylinder that slidably engages the internal surface of port 100. The introducer may have a distal end in the form of a conical atraumatic tip to allow for insertion into the sulcal folds of the brain. Port 100 has a sufficient diameter to enable bimanual manipulation of surgical tools within its annular opening such as suctioning devices, scissors, scalpels, and cutting devices as examples.

Port-Based Surgery

FIG. 1 is a diagram illustrating components of an exemplary surgical system used in port based surgery. FIG. 1 illustrates a navigation system 107 having an equipment tower 101, tracking system 113, display 111 (for a graphical user interface), an intelligent positioning system 175 and tracking markers 165 used to track medical instruments or an access port 100. Tracking system 113 may also be considered an optical tracking device or tracking camera.

In FIG. 1, surgeon 103 is resecting a tumor in the brain of a patient 106, through port 100. External scope 104, attached to automated arm 102, is typically used by the surgeon to enhance visibility of the brain at the distal end of the port 100. The external scope 104 may be zoomed-in or zoomed-out, and its output depicted on a visual display 111 which may be overlaid with a virtual imaging feed of virtual data contained in the field of view of the external scope 104. The data may include various overlays to identify sections of the registered brain to improve identification of tumor and tract margins by the surgeon and reduce damage to the functionality of the patient's neural connections.

Tracking and Navigation System

Active or passive fiduciary markers 267 may be placed on the port 100 (such as shown in FIG. 2A and FIG. 2B) and/or imaging sensor 104, and/or any medical instruments 216 to determine the location of these objects using the tracking camera 113 and navigation system. These markers 267 may be reflective spheres configured to be seen by the stereo camera of the tracking system to provide identifiable points for tracking. A tracked instrument in the tracking system is typically defined by a grouping of markers 267, which are used to determine the spatial position and pose of the volume of the tracked instrument in three dimensions. Typically, in known exemplary tracking systems a minimum of three spheres are required on a tracked tool to define the instrument, however it is known in the art that the use of four markers is preferred. For example optical tracking markers 267 shown in FIG. 2A and FIG. 2B.

Markers 267 may be arranged statically on a target on the outside of the patient's body or connected thereto. Tracking data of the markers acquired by the stereo camera are then logged and tracked by the tracking system. An advantageous feature is the selection of markers that can be segmented easily by the tracking system against background signals. For example, infrared (IR)-reflecting markers and an IR light source from the direction of the stereo camera can be used. Such tracking system is known, for example, such as the "Polaris" system available from Northern Digital Inc.

In a preferred embodiment, the navigation system may utilize reflective sphere markers in combination with a stereo camera system, to determine spatial positioning and pose of the medical instruments and other objects within the operating theater. Differentiation of the types of objects and their corresponding virtual geometric volumes could be determined by the specific orientation of the reflective spheres relative to one another giving each virtual object an individual identity within the navigation system. This allows the navigation system to identify the medical instrument or other object and its corresponding virtual overlay representation. The location of the markers also provides other useful information to the tracking system, such as the objects central point, central axis, orientation, and other information related to the object.

Other types of markers that could be used radio frequency (RF) markers, electromagnet (EM) markers, light emitting diode (LED) markers that may be pulsed or un-pulsed, glass spheres, reflective stickers, unique structures and patterns, where the RF and EM would have specific signatures for the specific tools they would be attached to. The reflective stickers, structures and patterns, glass spheres, LEDs could all be detected using optical detectors, while RF and EM could be picked up using antennas. Advantages to using EM and RF tags would include removal of the line-of-sight condition during the operation, whereas using an optical-based tracking system removes the additional noise and distortion from environmental influences inherent to electrical emission and detection systems.

Stimulation Probe

Figure 3B:
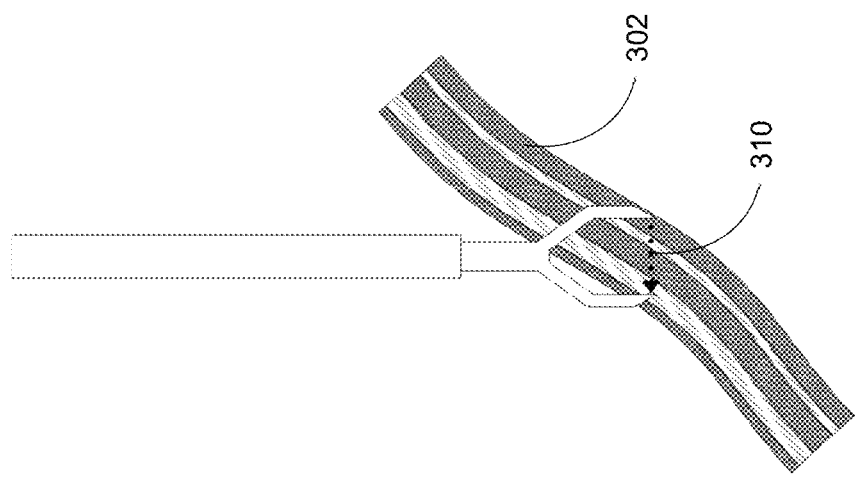
FIG. 3A and FIG. 3B Illustrates a presently used bipolar stimulation surgical tool.
Figure 3A:
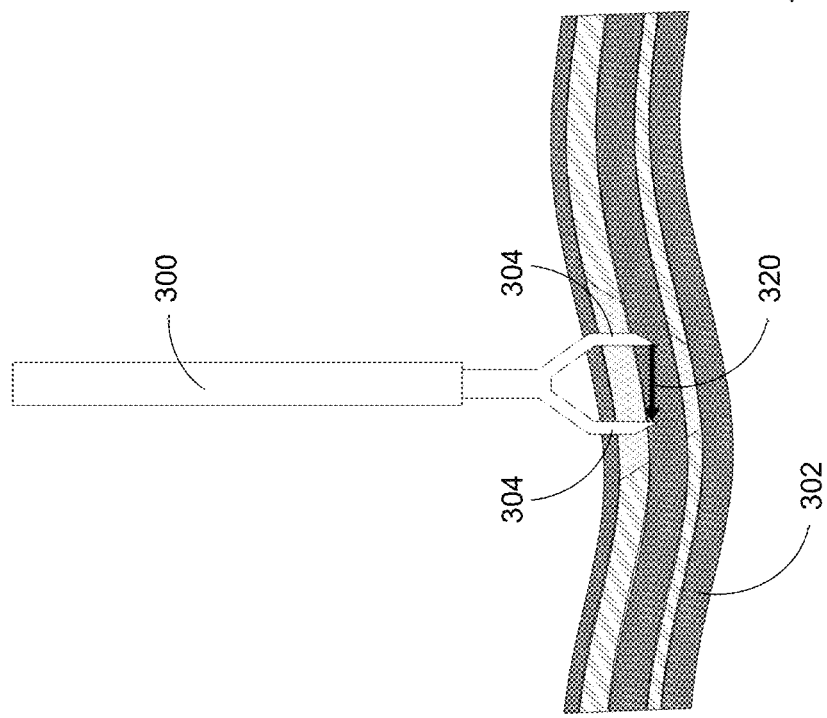

FIG. 3A and FIG. 3B illustrates a stimulation probe 300 that is presently employed in the art for performing functional stimulation. The illustrated apparatus 300 is the most commonly used in the industry and is termed a bipolar stimulation probe. These bipolar probes 300 produce a potential across their prongs 304 that when placed in contact with a white matter tract 302 induce a current through the tract that may stimulate the neural tract and cause a functional response in the patient. As shown in FIG. 3A and FIG. 3B the electrical resistance of the tracts is dependent on the linear direction of the potential across the two prongs, where the leftmost diagram shows low resistance 320 along the axial direction of the tract 302 and the rightmost diagram shows a greater resistance 310 when the potential is applied orthogonally to the axial direction of the tract 302.

Stimulation Port/Conduit

Figure 4B:
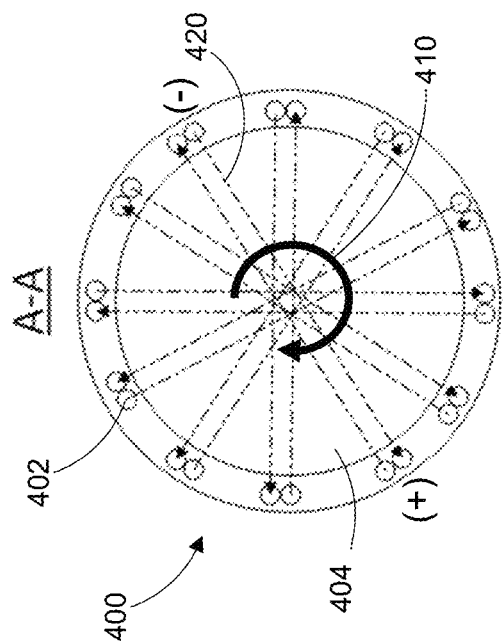
FIG. 4A and FIG. 4B Illustrates an embodiment of the stimulation apparatus as disclosed herein.
Figure 4A:
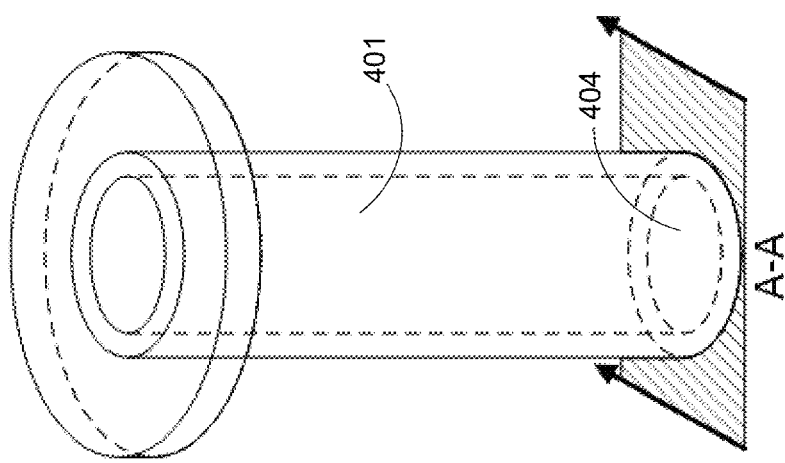

FIG. 4A and FIG. 4B depicts an example embodiment of the apparatus as disclosed herein. The stimulation port apparatus 401 in this embodiment is formed of a port such as that described above, embedded with a stimulation array on its bottom surface A-A. In this embodiment the stimulation array is shown as 400 in the cross-section view of the bottom surface of the apparatus A-A. The array may be formed of electrical stimulation terminals 402 aligned radially 410 around the distal opening of the conduit 404, with each terminal having a corresponding terminal of opposite polarity. In an alternative embodiment, not shown, the stimulation terminals may be embedded radially in the side of the port rather than the bottom surface.

In an embodiment, when the stimulation port apparatus 401 is functioning, only a single pair of corresponding terminals may be activated at any given time. This will allow for the apparatus to produce a linear electrical potential across the two active terminals of opposite polarity, such as that represented by arrow 420. In addition this apparatus may allow for the potential direction to be varied radially, for example the direction 410, or in any relevant geometry as needed by the user. Although the illustrated embodiment in FIG. 4A and FIG. 4B shows pairs of terminals at each radial location along the circumferential structure of the bottom of the apparatus it should be noted that a single terminal could be used as long as an electrical system is in place to allow its polarity to be changed as required. In addition the shape of the conduit need not be circular but may take the form of any desired shape such as a triangular prism, octagonal prism, rectangular prism, and etc.

Figure 5:
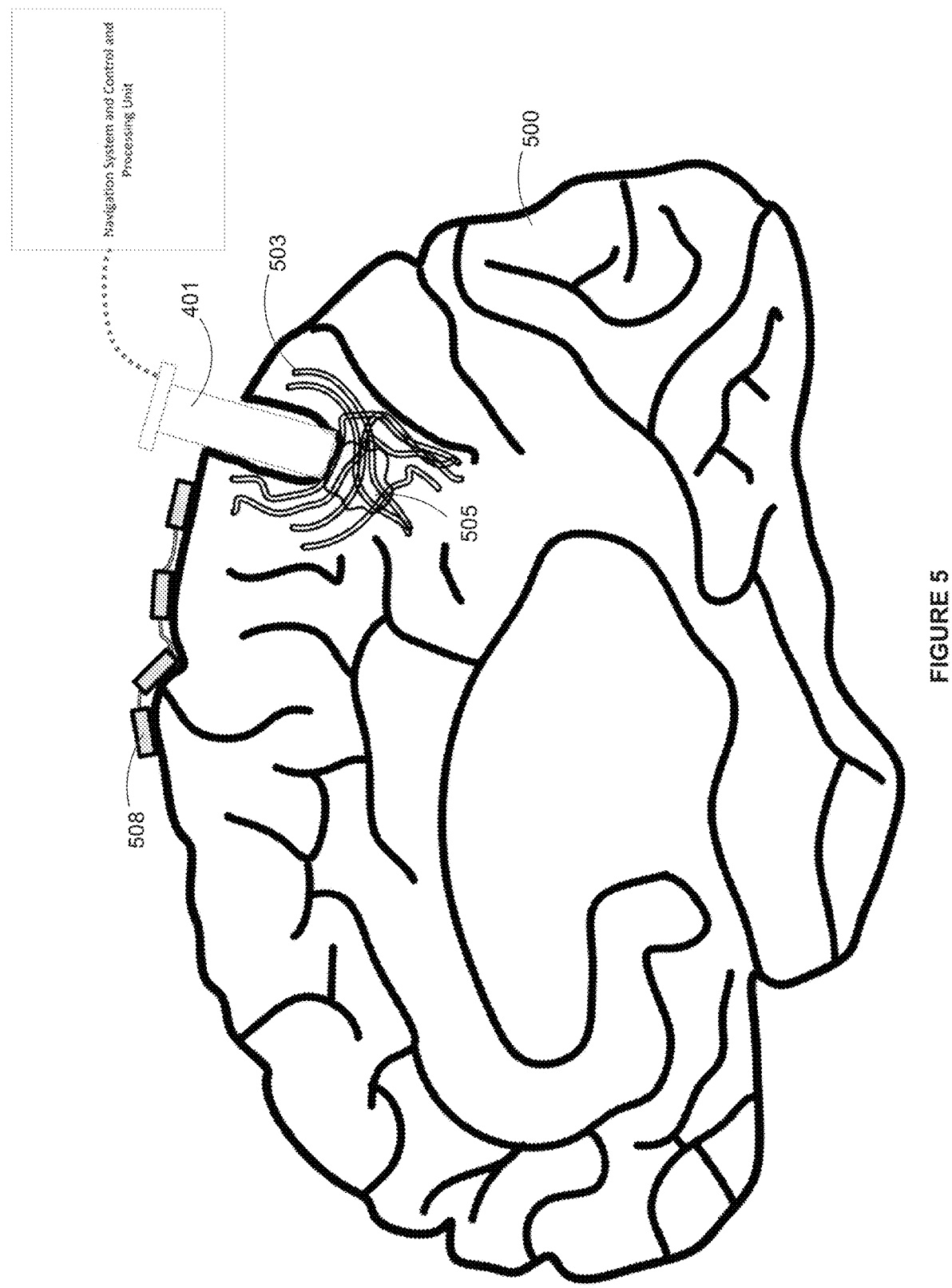
FIG. 5 Illustrates a surgical procedure employing the stimulation apparatus.

The apparatus as shown in FIG. 4A and FIG. 4B is particularly advantageous when used during a port based procedure such as that shown in FIG. 1, a more detailed diagram of which is depicted in FIG. 5. During this type of procedure, an area within the brain to be removed, such as a tumor 505 shown in FIG. 5, is approached through the insertion of an access port. The area is then subsequently removed through dissection and retraction of the tissue using specified medical instruments. During the removal, any tissue that may provide critical functions to the patient, such as movement or cognitive ability such as speech, is generally avoided so the patient may retain a higher quality of life post-surgery. However determining which sections of tissue are related to critical functions is generally a difficult task, and may in some cases be addressed by functional stimulation. An embodiment of the apparatus as depicted in FIG. 4A and FIG. 4B may allow a surgeon to perform functional stimulation so that the critical areas to be avoided can be determined intraoperatively and in real time while in the resection cavity, without requiring the surgeon to further implement additional medical instrumentation in the area being resected. For example in FIG. 5, the stimulation port apparatus 401 is already deployed in the surgical cavity of the patient's brain 500 and is in contact with the tissue of interest, including both the tissue to be removed 505 and the functional tissue (such as the tractography 503) to be avoided. Thus to determine if the section of the tissue of interest the surgeon will subsequently be removing from the patient's brain 500 is in fact related to a critical function of the patient, the surgeon merely has to stimulate the tissue section to be removed using the stimulation port apparatus 401, and test the patient's critical functions. This may be contrasted with presently employed methods where either the stimulation or cortical mapping is performed prior to the resection surgery in a separate surgery, or an additional probe such as 300 depicted in FIG. 3A and FIG. 3B, is deployed in the cavity to perform the stimulation intraoperatively. The apparatus is also useful in other procedures where stimulation of neuronal tracts can be used to identify critical tissues, for example in spinal surgery. Thus combining a functional stimulation array with a surgical conduit, such as in the stimulation port apparatus 401 shown in FIG. 4A, may benefit a surgeon by allowing them to perform stimulation on the fly, saving time and potentially preventing the deployment of an additional device in the cavity.

Monopolar Probe

Figure 6:
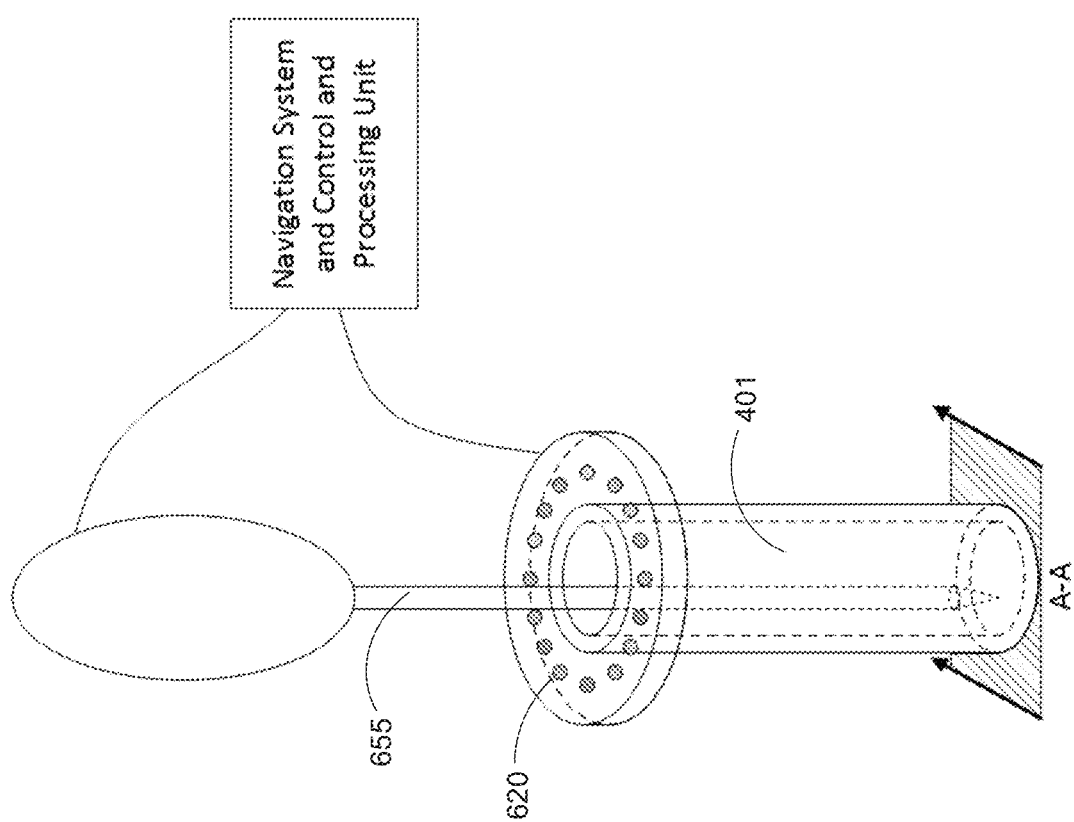
FIG. 6 Illustrates a diagram of an alternate embodiment of the stimulation apparatus as disclosed herein.
Figure 7:
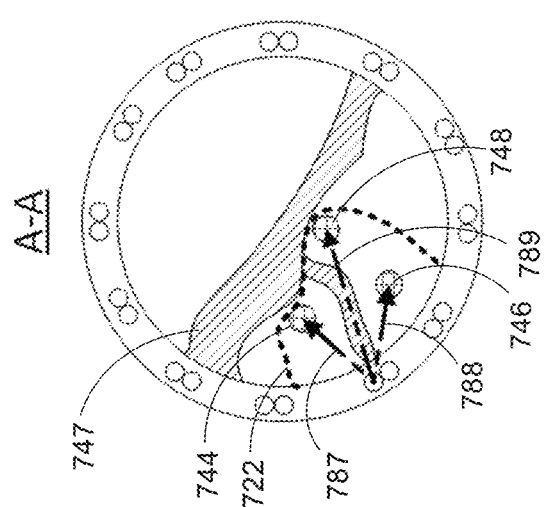
FIG. 7 Illustrates a cross sectional view of the distal end of the alternate embodiment of the stimulation apparatus shown in FIG. 6.

In an alternate embodiment the stimulation port apparatus 401 described above may be used in conjunction with a monopolar probe such as 655 shown in FIG. 6 that would allow the surgeon to create a stimulation current in the direction between the monopolar probe 655 and an activated stimulation terminal of opposite polarity located on the bottom surface of the stimulation port apparatus 401. For example, as shown in the cross section view A-A of FIG. 7, where the monopolar probe location 744 is shown in the cross sectional area. In the cross section, a stimulation current 787 is being applied from an active terminal located on the bottom cylindrical surface area of the stimulation port apparatus 401 to the monopolar probe's tip location 744. This embodiment would allow the surgeon to further define the directional customization of the stimulation current which may provide beneficial information to the surgeon in various situations. For example, the surgeon could probe different sections of the tissue in the accessible region at the bottom of the stimulation port apparatus 401 to determine which sections are ones that correspond to functional areas and to avoid those sections. Referring to the cross section A-A, given that the shaded area 747 is a functional area to be avoided and the surgeon is aware that such an area exists at the tissue of interest, the surgeon may probe multiple points such as points 744, 746, and 748 to determine the boundary of said area 747. For example, after probing the points, it would be apparent that the stimulation current 789 passed through the functional area 747 given the response of the patient confirmed such a stimulation, while the remaining stimulation currents 787 and 788 could be assumed to not have passed through the functional area 747. Such an assessment allows the surgeon to infer the approximate location of the functional area 747 relative to its neighboring areas at least in the region (shown by the dashed line 722) where the stimulation was applied. It should be noted that the functional area 747 may not be so visible in actual brain tissue when a neurosurgery is being performed, thus being able to differentiate such an area during a procedure may be beneficial to the surgeon. In addition, if the surgeon believes that the area outlined by the dashed line 722, as a result of a visual inspection, is of a tissue type to be removed, confirmation that no functional areas such as 747 exist in this region becomes an important step allowing the surgeon to confirm that their visual inspection of the surgical area is correct. This further provides a potential benefit to the surgeon utilizing this embodiment of the apparatus shown in FIG. 6.

In another embodiment, the stimulation port apparatus 401 may be embedded with LED's 620 or other indicator elements at its proximal end (visible to the surgeon when performing surgery) to indicate to the surgeon which stimulation terminal(s) located on the distal end of the apparatus is active. This may allow them to aim the stimulation current in the desired direction, as without an indication as to which terminal is active the surgeon may find it difficult to determine in which direction the stimulation current (such as 787) would be travelling, thus rendering it difficult to infer the areas of the tissue of interest to be removed. These LED's may be installed in any common way known in the art and may be configured and powered by an external wired source such as the Navigation System and Control Processing Unit shown in FIG. 6. In addition the activation and deactivation of the stimulation terminals located on the bottom of the apparatus may also be configured and powered by the Navigation System and Control Processing Unit shown in FIG. 6. A further description of an exemplary Navigation System and Control Processing Unit and its implementation with respect to the embodiments of the stimulation port apparatus 401 will be discussed in further detail below.

Deformable Probes for Stimulation

FIG. 8 illustrates an additional embodiment of the stimulation port apparatus 401 where the stimulation prongs 800 are collapsible allowing them to deform on uneven tissue surfaces. This probe apparatus may be particularly useful when dealing with uneven tissue surfaces such as with tumors in the brain. They may alleviate a need for the surgeon to apply pressure to an uneven tissue with a stimulation apparatus in order to flatten out the surface for the application of a stimulation current, which could cause trauma to the particular elements being pressed flat and may in some cases cause irreparable damage to the patient's brain. In an embodiment, these collapsible stimulation prongs 800 may be connected to simple metallic springs 802 mounted within empty columns 804 in the hull 806 of the stimulation port apparatus 401. Although springs are described as the collapsible medium in the illustrated embodiment, it should be noted that other collapsible mediums such as pneumatic and sponge-like mechanisms may also be employed. However, in order for the embodiment of the apparatus employing electrical stimulation to still function the collapsible media must be able to at least conduct enough electricity to allow for a successful stimulation application to a patient. It should be noted that the stimulation terminals as described above may be connected to a stimulation terminal control processor such as methods described in U.S. Pat. No. 7,164,951 "ELECTRICAL CONNECTOR ASSEMBLY HAVING INTEGRATED CONDUCTIVE ELEMENT AND ELASTOMERIC SEAL FOR COUPLING MEDICAL LEADS TO IMPLANTABLE MEDICAL DEVICES" which is herein incorporated by reference in its entirety.

Port with Integrated Electrocorticography (EcoG) Sensors

Figure 9B:
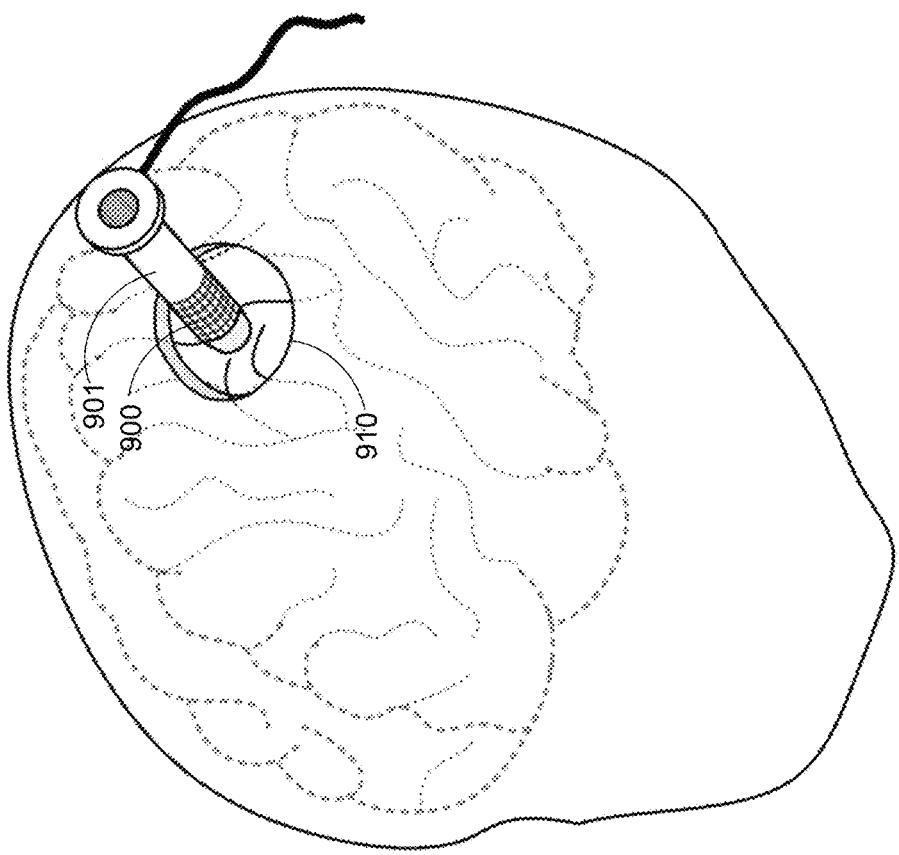
FIG. 9A and FIG. 9B Illustrates the use of an ECoG grid on a patient and the use of a stimulation apparatus with built in ECoG grid in a patient.
Figure 9A:
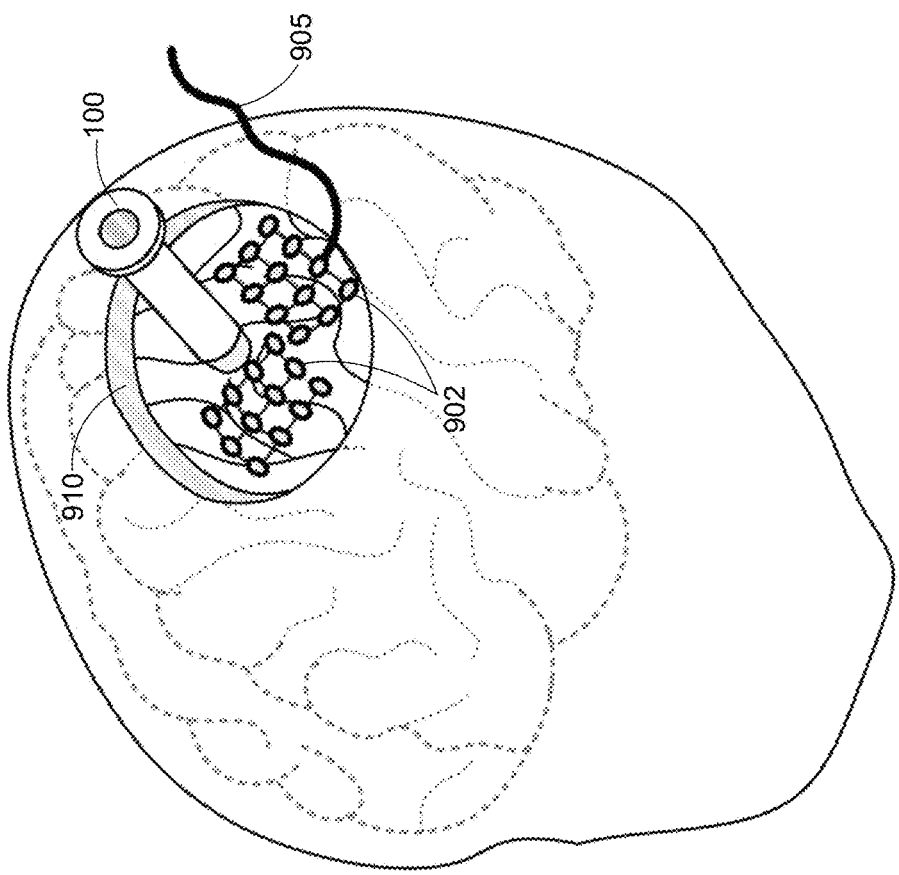
Figure 10:
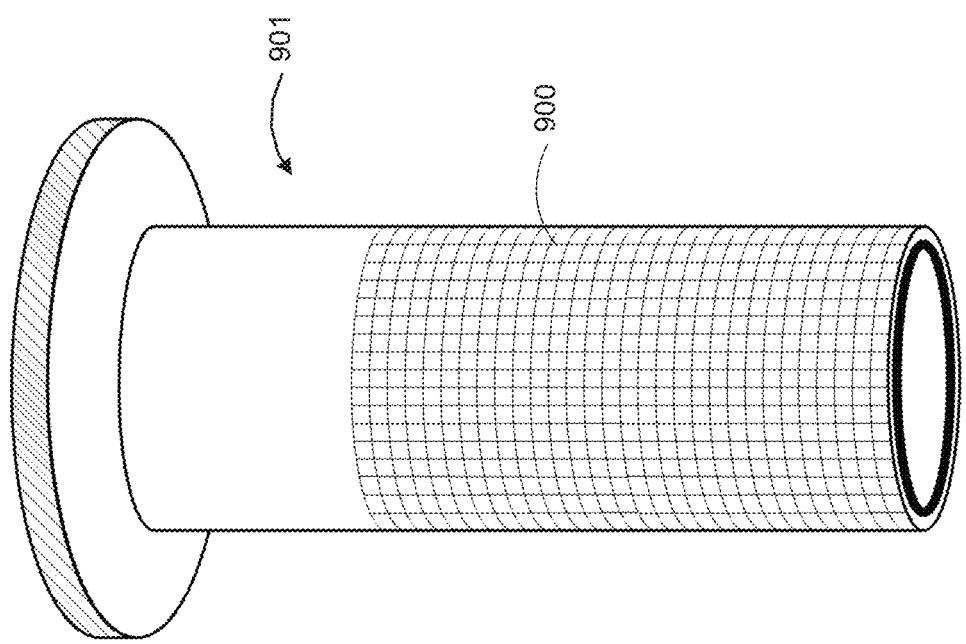
FIG. 10 Illustrates an access conduit apparatus with built in ECoG grid.

One present use of ECoG sensors are their intraoperative application during cranial resection surgeries such as the "Montreal Procedure" in which they are used to ensure that an entire epileptogenic zone being resected from a patient is removed. Another general use of ECoG is to detect for after discharges during cortical mapping procedures. Cortical mapping procedures involve stimulating different regions of a patient's brain and determining their function. Specifically these procedures involve mapping the different functional areas of a patient's brain so they can be prioritized and avoided if necessary. The ECoG sensors in these exemplary procedures are generally placed on the upper surface of the patient's brain as an array for example as shown as EcoG sensor grid 902 in FIG. 8. Thus, the sensors are generally spaced away from the origin of the signal they are to detect. During a cortical mapping procedure the detection of an after discharge generally signifies to the surgical team, that any functional response detected during the previous stimulation interval should be considered invalid. This is due to the after discharge being an indicator of an induced epileptic neural response of the patient to the applied stimulation as opposed to a normal stimulation response induced by the stimulation device. In the case of the "Montreal Procedure" the electrodes are utilized during resection to ensure that the epileptogenic zone is entirely resected by detecting for any post resection epileptic neural activity. The resection phase of the "Montreal Procedure" may be performed using the port based methodology described above such as shown in FIG. 8, where the ECoG sensor grid 902 is placed on the superficial brain surface and the port 100 is used to resect the epileptogenic zone of the patient's brain. In an embodiment, the ECoG sensor grid 902 generally used for neural activity detection may be integrated with the access port 100 as opposed to being installed on the superficially exposed brain surface of the patient's brain. For example, ECoG sensor grid 900 is located on the ECoG port apparatus 901 shown in FIG. 9A and FIG. 9B and FIG. 10. This may be advantageous in that it may reduce the size of the craniotomy needed to perform the surgery, resulting in a less traumatic surgery to the patient. This is illustrated in FIG. 9A and FIG. 9B where the left diagram employing an ECoG sensor grid 902 and a port 100 for a functional procedure requires a larger craniotomy 910 than the craniotomy 910 in the right diagram, employing the ECoG port apparatus 901. In addition this apparatus may also allow for the reduction in the number of medical instruments required to perform the surgery, potentially resulting in a timelier and more orderly, neurosurgical operation. Furthermore, since the resection cavity created during the application of the port based surgical methodology described above is nearer the region of the brain to be operated on than presently used ECoG sensor grids, the ECoG port apparatus 901 may improve the detection of after discharges or epileptic seizure events. This improvement may result from the reduction in distance of the ECoG sensor grid 900 located on the ECoG port apparatus 901 from the origin of the electrical brain activity (i.e. after discharge or epileptic seizure event). In addition the reduction in distance may also allow the ECoG port apparatus 901 to detect the neural response signals at a lower threshold (i.e. lower energy signals will be detected) because the signals do not have to propagate through as much brain tissue as with a conventional ECoG sensor grid 902. This lower detection threshold may potentially reduce the time it takes to confirm that either no discharge is detected and a successful resection of the epileptic region was performed, or that an after discharge was detected.

The integration of the ECoG electrode grid 900 onto the surface of the access port 100 may be achieved by simply embedding the grid onto the surface using common techniques as are known in the art such as circuit printing and adhesion techniques. The ECoG port apparatus described here and illustrated in FIG. 9A and FIG. 9B is an exemplary embodiment and it is to be understood that variants of the embodiment shown may be used.

The ECoG electrode grid 900 when integrated in the ECoG port apparatus 901 may be connected via electrical wiring 905 to an ECoG processor (not shown), as is known in the art, to be processed and the results displayed to a user. Although the embodiment shown in FIG. 9 has a wired ECoG grid, in some embodiments an ECoG signal processor (not shown) may be mounted directly onto the ECoG port apparatus 901 and connected to the grid directly to allow for wireless transference of relevant ECoG information.

Combination of Stimulation and Sensor Apparatus

Figure 11:
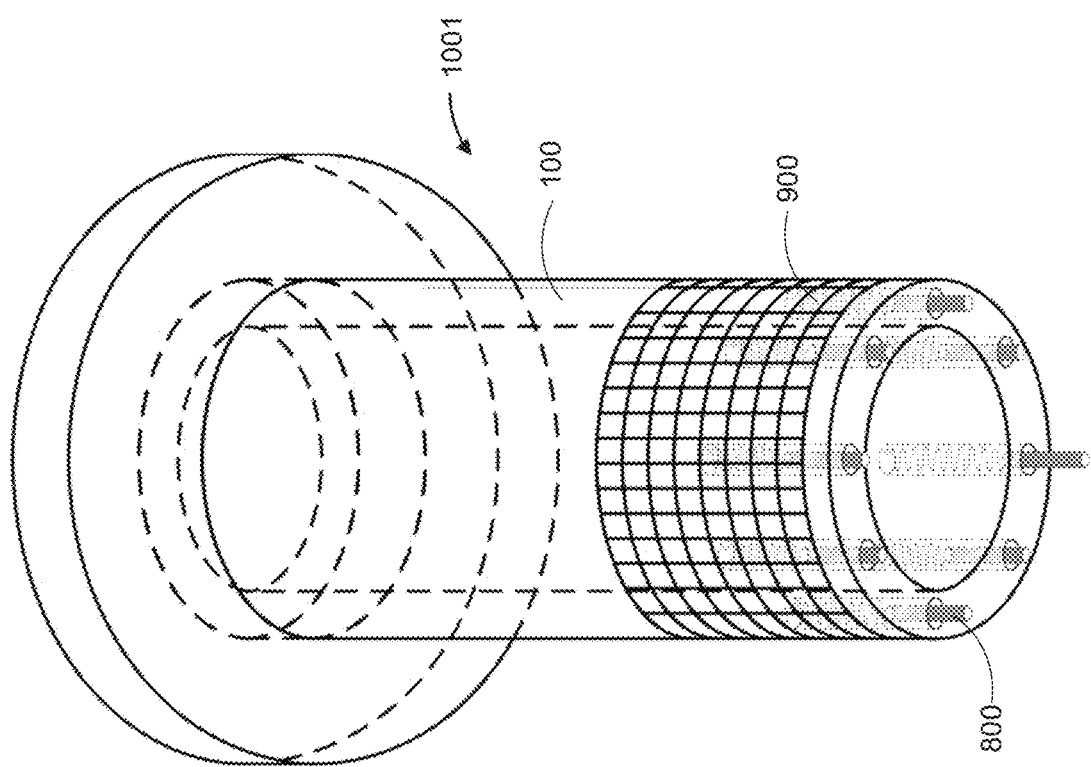
FIG. 11 Illustrates the stimulation apparatus with built in ECoG grid and deformable stimulation probes.
Figure 12A:
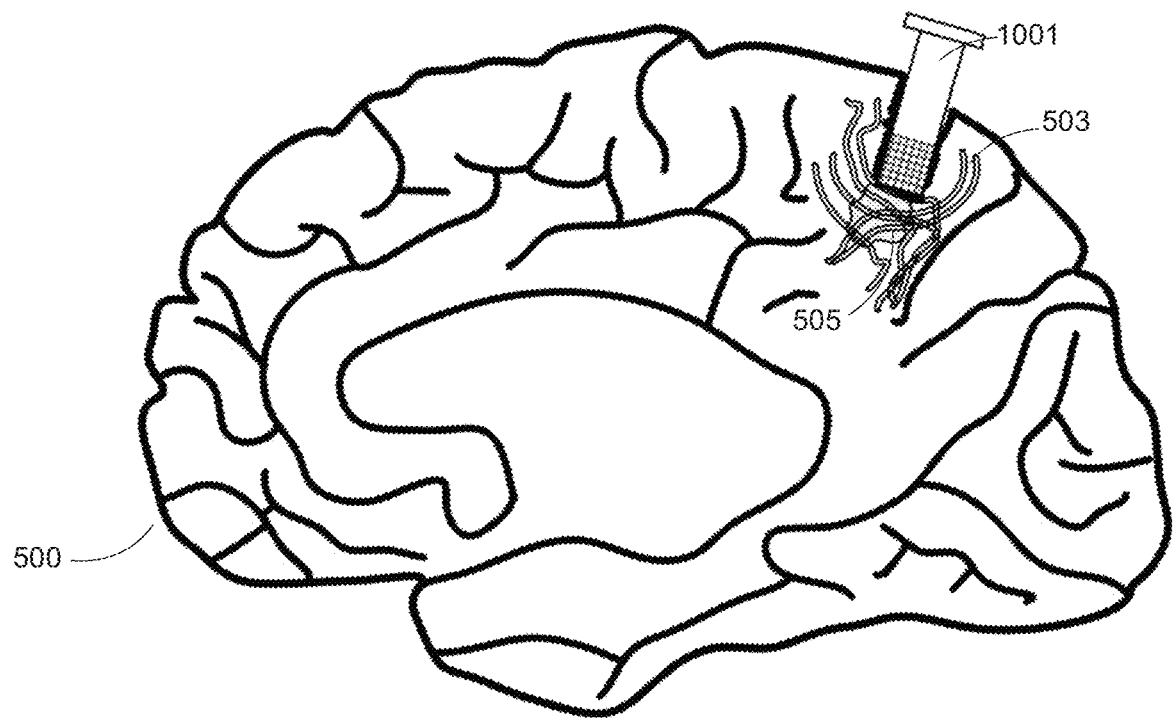
FIGS. 12A and 12B Illustrates the use of the stimulation apparatus with built in ECoG grid during an intracranial procedure.

In an additional embodiment, the port 100 may be situated with both stimulation electrodes and an ECoG grid. For example, the ECoG stimulation port apparatus 1001 shown in FIG. 11 is formed of a port 100 embedded with both a stimulation terminal array 800 as well as an ECoG sensor grid 900. In an embodiment the apparatus may benefit the user by allowing a user to perform a procedure through its access tube while simultaneously allowing the surgeon to stimulate and map tract functionality during a surgery. In particular during resection type procedures such as brain tumor resection or a "Montreal Procedure" as described above, combining an access port/conduit with both stimulation terminals and ECoG sensors is of a greater potential benefit than employing either of the previously described stimulation port apparatus 401 or an ECoG port apparatus 901 separately. By utilizing either apparatus separately both may require an additional medical instrument to correctly perform the surgery. For instance, using the stimulation port apparatus would require the need for an ECoG grid, to validate any successful stimulation applications to the patient's brain. On the other hand using the ECoG port apparatus would in some applications require the need for a stimulation probe to correctly map the functional areas of a patient's brain. FIG. 12A shows the same procedure shown in FIG. 5, but with the stimulation port apparatus 401 switched out for the stimulation ECoG port apparatus 1001. Whereas in the procedure shown in FIG. 5 the surgeon would have to install an ECoG grid 508 on the surface of the brain 500 to validate the patient's functional responses, in the case shown in FIG. 12A the ECoG grid has been supplied by the stimulation ECoG port apparatus 1001. It should be apparent that any potential advantages from the uses of the stimulation port apparatus 401 and the ECoG port apparatus 901 may also be inherent advantages provided by the stimulation ECoG port apparatus 1001. In some instances the stimulation ECoG port apparatus 1001 provides a further advantage above and beyond that of the prior mentioned two apparatuses (i.e. 401 and 901) in that the reduction of three tools, namely an access port/conduit, a stimulation probe, and a ECoG sensor grid greatly reduces the occupied space in and around the surgical area where an operation is being performed. In addition the combination may also benefit the user in providing a simpler apparatus to implement during a procedure.

Figure 12B:
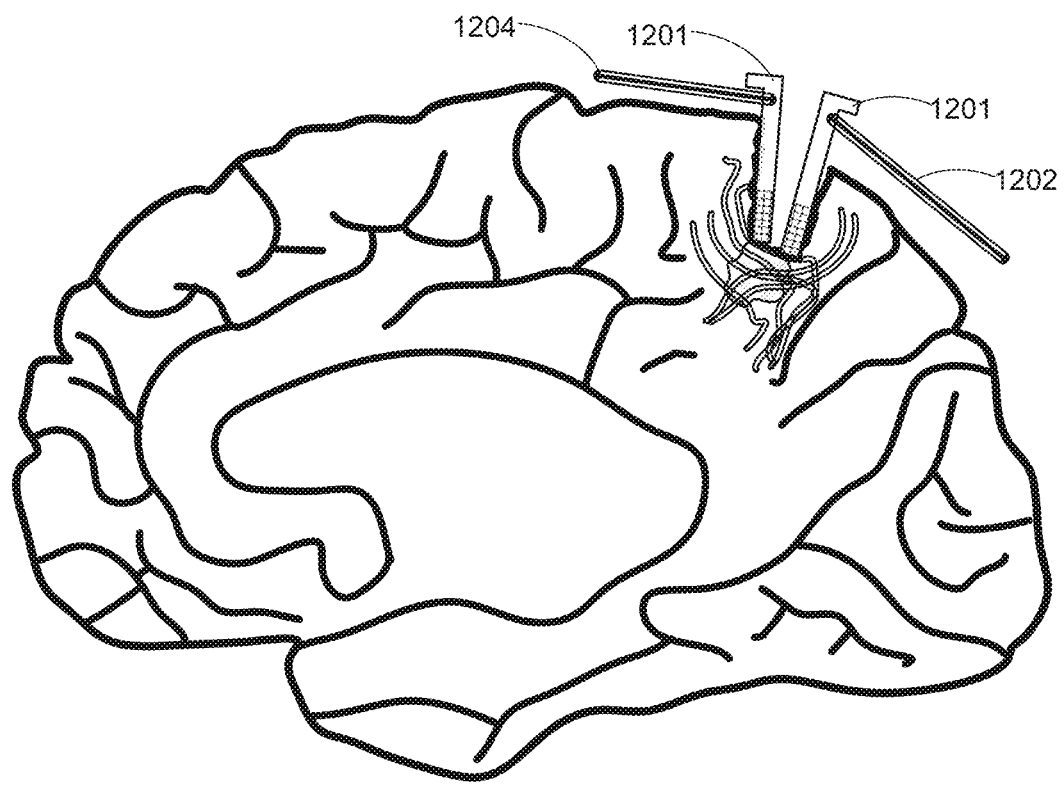

In an alternate embodiment, such as that shown in FIG. 12B, retractors 1202 may be used in place of the access port. In this embodiment the retractors 1202 are embedded with both ECoG sensors as well as stimulation terminals using the same methods as for use with the access port. Retractors are commonly used with ancillary mounting systems 1204 (partially shown) and the wiring for the ECoG and stimulation terminals may be wired through these mounting systems given that the retractors are wired. However other variations may also be contemplated. The internal design of these retractors may in some embodiments be equivalent to those shown in FIG. 15, where instead of showing a cross section of an embodiment of the stimulation port ECoG apparatus as described below the view shows an elevated side view of the retractor (in this case a semi-cylinder shape) having the same components as the embodiment. Indeed the retractor in some instances may be formed as half the access port, with the split taken across a bifurcating plane such as 1310 shown in FIG. 13. However in such cases it would be known to those in the art that minor modifications would be needed to form the retractor in a surgically safe manner, such as smoothing the edges to avoid unintentionally damaging tissue which may come into contact with the described embodiment of the apparatus. Using retractors in place of the access port may be useful in cases where open surgery is performed and a larger access area is needed or when a surgeon determines it more beneficial to use such an approach.

Figure 13:
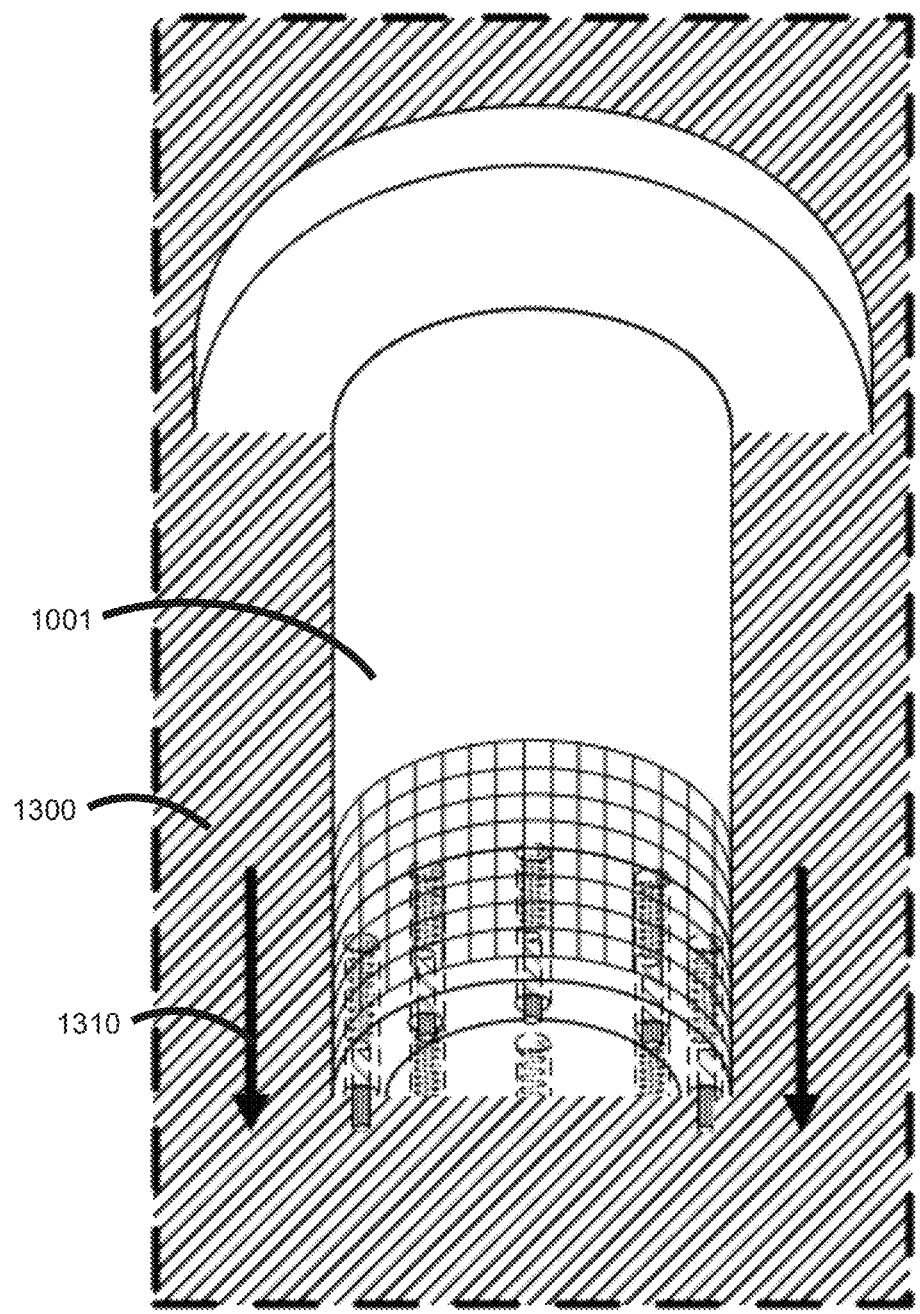
FIG. 13 Illustrates a cross sectional plane about which a cross section of the stimulation ECoG port apparatus is taken and shown in FIG. 13.
Figure 14:
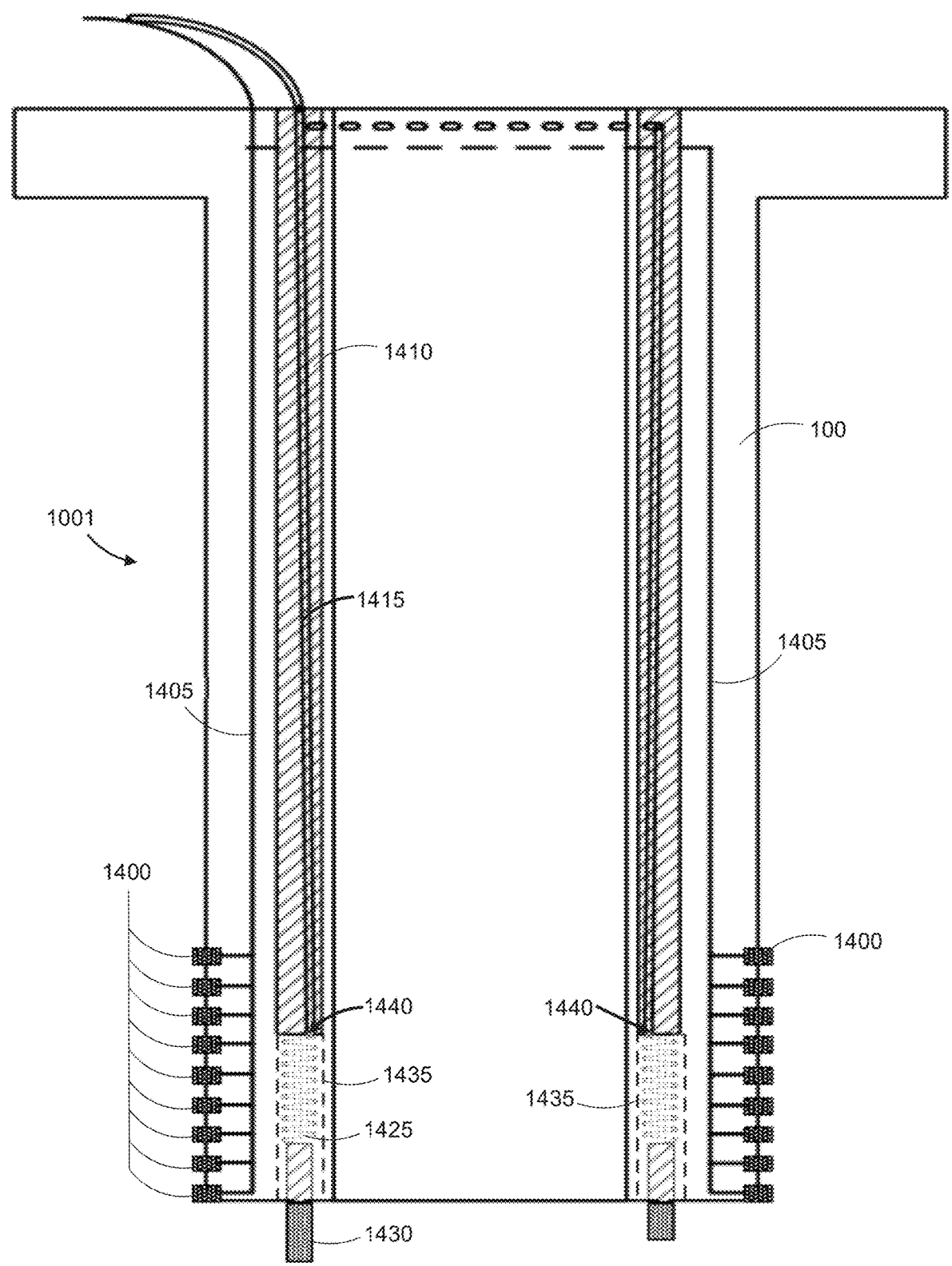
FIG. 14 Illustrates the cross section as taken from FIGS. 12A and 12B.
Figure 15:
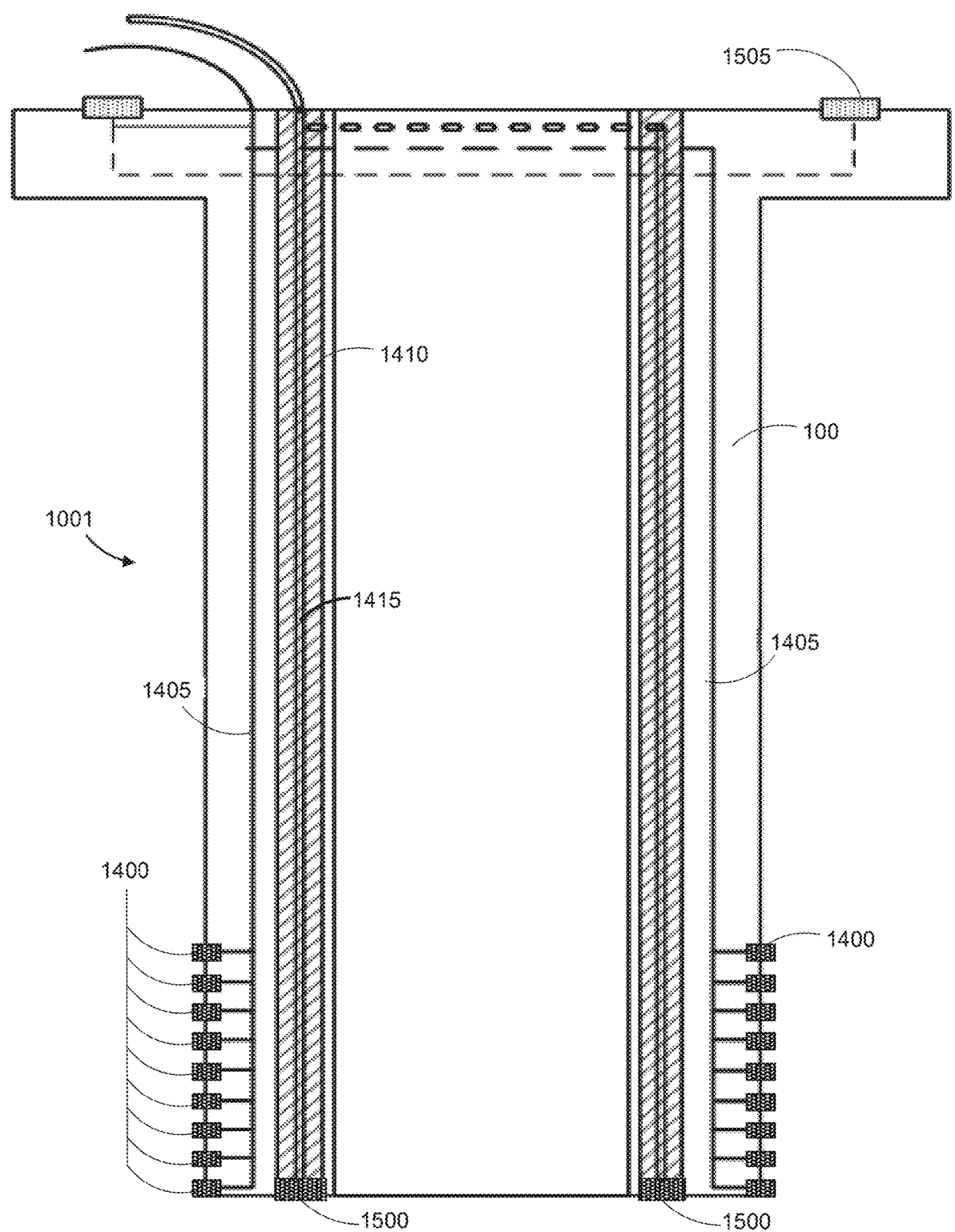
FIG. 15 Illustrates an alternate embodiment of the cross section of the stimulation ECoG port apparatus taken from FIGS. 12A and 12B.

FIGS. 13, 14, and 15 illustrate the internal system structure of an embodiment of the apparatus as disclosed herein and will be described as follows. FIG. 13 depicts the stimulation ECoG port apparatus 1001, about which a plane 1300 defining a cross sectional view in the direction of the arrow 1310 is taken and displayed in FIG. 14. In the cross sectional view in FIG. 14, the ECoG electrode grid is made up of ECoG sensors 1400. These ECoG sensors may be structurally integrated with the port 100 by commonly known mounting techniques such as circuit printing or adhesion techniques, in a grid type configuration. An ECoG control system may then be connected to this grid through the multi-wire cable 1405 and used to control its real time configuration parameters. Some non-limiting examples of controllable configuration parameters are frequency, voltage, sampling rate, amperage, waveform, polarity, lower limit and sensitivity. It should be noted that some of these parameters may be applicable to electrical stimulation and others applicable to detection of electrical signals within the brain and some applicable in both cases. The stimulation ECoG port apparatus 1001 also has elongated cavities 1410 for the stimulation electrodes. At least two different embodiments of stimulation electrodes may be implemented in combination with this cavity and are shown in FIG. 14 and FIG. 15 respectively. FIG. 14 depicts a more complicated stimulation terminal assembly 1435 involving the use of deformable stimulation terminal prongs 1430 as described above, while FIG. 15 depicts a simple stimulation terminal configuration 1500. The deformable stimulation terminal 1435 is formed from a spring 1425 connected at its distal end 1440, to or within the cavity 1410, and connected at its proximal end to the stimulation terminal 1430. The stimulation terminals 1435 may be controlled via the multi-wire cable 1415 connected to a stimulation terminal controller as is known in the art, and is further connected to the stimulation terminals 1435 at point 1440 which may be seen in the cross section depicted in FIG. 14. The simple stimulation terminal 1500 may be formed by embedding an electrode or other stimulation mechanism at the proximal end of the cavity 1410, in a similar manner in which the ECoG sensors 1400 are embedded in the wall of the port 100. These stimulation terminals, similar to the deformable stimulation terminals 1435, may be controlled via the multi-wire cable 1415 connected to a stimulation terminal controller as is known in the art, and is further connected to stimulation terminals 1500. An additional feature of the stimulation apparatus depicted in FIG. 15 is the embedded LED's 1505 that may be employed to identify the direction of stimulation application to a user. Both the embodiments of the deformable stimulation terminal and the simple stimulation terminal may be in an embodiment formed of electrodes capable of applying a stimulation current/voltage at the point of contact with the tissue.

Advantages of Stimulation and Sensor Apparatus with Navigation System

A potential benefit that may be derived from employing the apparatus disclosed may be the use of the apparatus in determining an optimal direction to apply a stimulation current to the tissue of interest. Being able to determine the optimal direction of a stimulation current application with respect to a tissue being stimulated may potentially benefit the patient by reducing the chance of a harmful stimulation application. Further in an additional embodiment, the apparatus may be used in combination with a navigation system, whereby the linear direction of the stimulation current produced by the apparatus may be automatically determined relative to the tissue being stimulated (for example white matter tractography in the brain) for maximum effect. An additional embodiment enabled by the use of the apparatus with a navigation system would be the ability to map any functional information acquired from a stimulation to preoperative or intraoperative imaging, thus further potentially benefiting the user. In yet a further embodiment, if the apparatus is used in combination with the navigation system and an informatics engine, the informatics engine may be able to provide better choices of stimulation trains (i.e. frequency, duration, phase, wave shape, and amplitude) to the user when they are operating within specific functional areas of the brain. A detailed description of a system having navigation and informatics capabilities is outlined in international publication No. WO/2014/139021, titled "INTRAMODAL SYNCHRONIZATION OF SURGICAL DATA" which is hereby incorporated by reference in its entirety. The potential embodiments described above will be elaborated on in further detail as follows.

Independent Tractography Direction Inference using Probe

As mentioned above an embodiment of this apparatus is that it may be used to infer the optimal direction of a stimulation application on a tissue of interest. More specifically when employing the apparatus in an embodiment where the apparatus is being used to stimulate a white matter fiber (tract) in the brain, the directionality of that tract may be determined using the apparatus without the use of pre-operative or intraoperative imaging.

Figure 16:
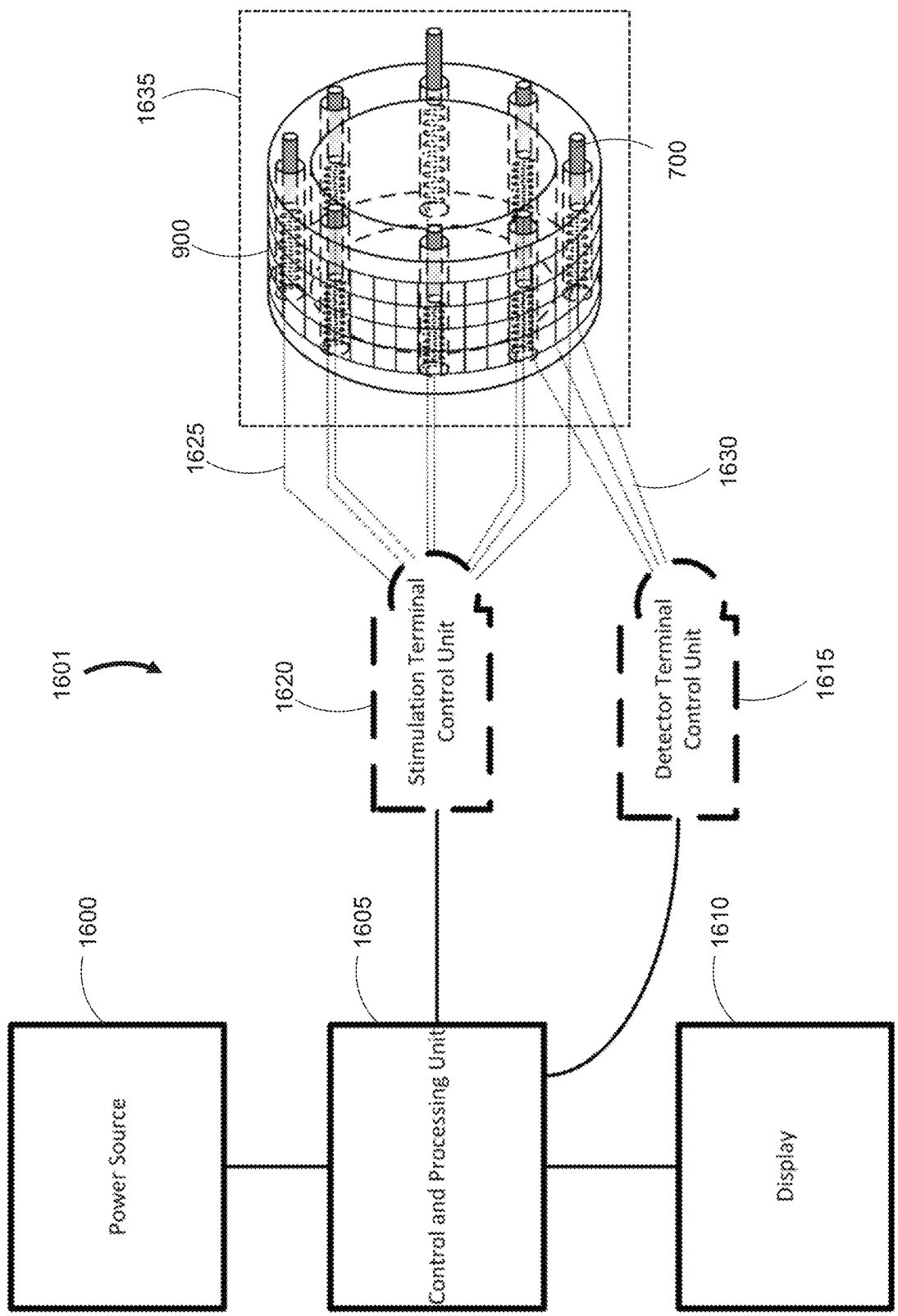
FIG. 16 Illustrates a block diagram of a generic stimulation system which may or may not employ the stimulation ECoG port apparatus.

An example of a system capable of determining tract direction is shown in FIG. 16. The stimulation system 1601 includes a control and processing unit 1605 generally used to configure the parameters and actions of the system, a display 1610 to display said parameters and actions to a user, a power source 1600 for powering the system, a stimulation terminal control unit 1620 to control the stimulation terminals of the system, a detector terminal control unit 1615 to control and elicit feedback from the ECoG and/or other sensor apparatuses employed by the system, and an embodiment of an apparatus 1635 as disclosed herein having stimulation terminals, which may be in the form of the stimulation port apparatus 401 or the stimulation ECoG port apparatus 1001 as described in further detail above. It should be noted that the apparatus 1635 of the stimulation system 1601 is provided as a diagrammatical representation of any of the applicable embodiments of the apparatus contemplated by this disclosure, the diagram showing only the systematic portions that connect within stimulation system 1601 depicted in FIG. 16. For example, the apparatus portion 1635 may represent the stimulation ECoG port apparatus 1001 shown in FIG. 15, where the connections 1415 connecting the stimulation terminals 1500 to the stimulation controller are equivalent to the stimulation terminals 700 and their connections 1625 to the stimulation terminal control unit 1620 in the embodiment of the stimulation system 1601 depicted in FIG. 16. Further the connections 1405 connecting the ECoG grid 1400 to the ECoG controller in the embodiment of the apparatus shown in FIG. 15 are equivalent to the connections 1630 connecting the ECoG grid sensors 900 to the detector terminal control unit 1615 of the embodiment of the stimulation system shown in FIG. 16.

The stimulation system 1601 shown in FIG. 16 may function in the following way. The processor 1605 may be programmed with instructions to run a particular functional stimulation acquisition sequence when prompted by a user, wherein an exemplary stimulation acquisition sequence may generally comprise: applying a stimulation current to the patient through one or more terminals, the stimulation current being configured with particular electrical parameters such as frequency, amperage, voltage, waveform, etc.; and acquiring response data from the ECoG sensors wherein the acquisitions correspond with the stimulation applications to validate, for example, a successful functional response by a patient as described in detail above. In order to perform the stimulations the control and processing unit 1605 may send instructions to the stimulation terminal control unit 1620, which may in turn activate the correct prongs 700 with the signal as determined by the programmed instructions. Simultaneously the control and processing unit may additionally send instructions to the detector terminal controller unit 1615 which may in turn activate the detection grid 900 and acquire data as per the programmed instructions.

The optimal direction for applying the stimulation current to a tract with respect to the prongs of an apparatus in the manner mentioned above may be determined as follows. By consecutively stimulating the area adjacent to the stimulating prongs of an apparatus as disclosed herein in different directions, wherein the area contains a tract, then subsequently acquiring the resulting electrical resistances across each of the directions, the optimal direction to apply the stimulation current may be determined as the direction having the least electrical resistance, where methods of determining the resistance across a pair of electrical terminals are known in the art.

For, example referring to the diagram of an embodiment of the apparatus depicted in FIG. 4, where the arrows 420 illustrate the potential direction of current flows. It is apparent that the linear potentials may be rotated radially by producing an electrical potential across prongs located circumferentially across from one another. This can be accomplished by applying potentials sequentially in a radial direction (such as 410 shown in FIG. 4) around the prongs of the apparatus. Each successive application of a stimulation current along the radial direction 410 may subsequently be followed by an acquisition of the resulting resistance of the tissue along each direction. Once the resulting resistances are acquired the data may be input into a processor for analysis or displayed to the user to be manually or automatically analyzed and the direction of the tract determined. The analysis would consist of finding the stimulation direction having the lowest resistance and assuming this direction was the direction of the tract.

Figure 17B:
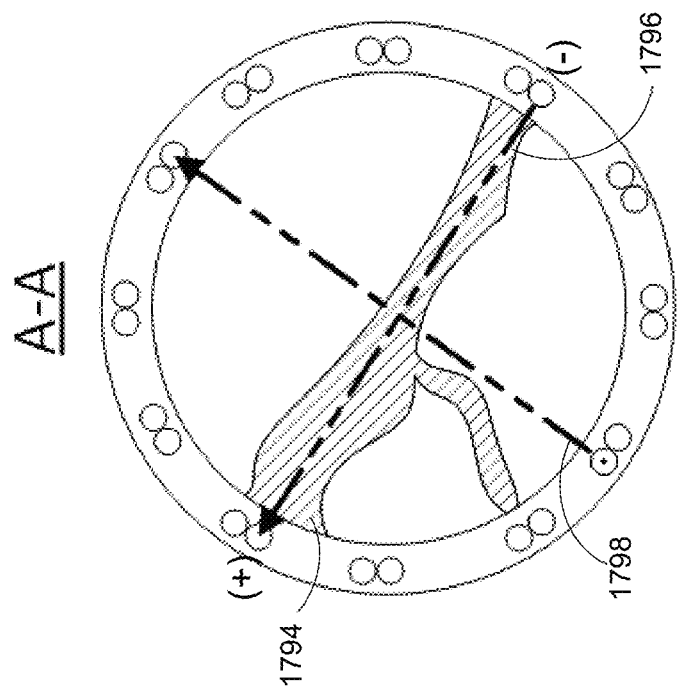
FIG. 17A and FIG. 17B Illustrates the stimulation of white matter bundles at the distal end of the stimulation ECoG port apparatus.
Figure 17A:
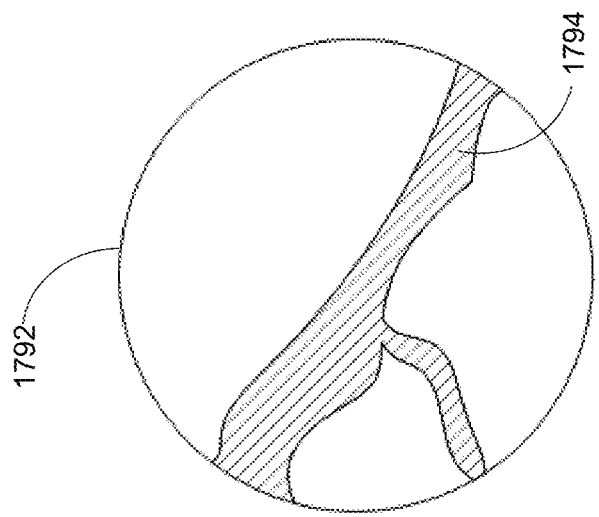

This analysis may be arrived at from the fact that fiber tracts (white matter nerve bundles) in the brain generally have a higher conductivity than surrounding tissue. For example, with reference to FIG. 17A, FIG. 17B, and FIG. 9B the potential across the path 1796 would be less, due to the presence of the tract 1794, than that across the path 1798. Such a result would allow the user or processor to infer the most probable directionality of the tract being stimulated (i.e. due to the tract 1794 likely having a potentially higher conductance then the surrounding tissue). The optimal direction for applying a stimulation current to the tract is determined by the calculation of the direction with the lowest resistance. It should be noted that the exemplary method provided is one manner in which a resistance analysis may be done, however other types of analysis taking into consideration the resistance and stimulation parameters applied and acquired by the system shown in FIG. 16 may be employed without diverging from the scope of the system and/or methods as disclosed herein.

Tractography Direction Inference using Probe Independently and with Low Probe Current An additional benefit of using the apparatus as disclosed herein to determine the tract direction is that the stimulation current used for determining the tract direction may be chosen to be low enough such that no functional response in the patient is detected. These particular stimulation pulses would be used solely to determine the direction of the tract and thus need not be at high enough amperage to elicit a response from the patient. Indeed, by not applying significant stimulation current, the patient may be prevented from experiencing detrimental results such as unneeded stimulation of the brain, further epileptic responses and, in the worst case, brain damage.

Use of Probe with Navigation System for Determining Tract Direction

Figure 18:
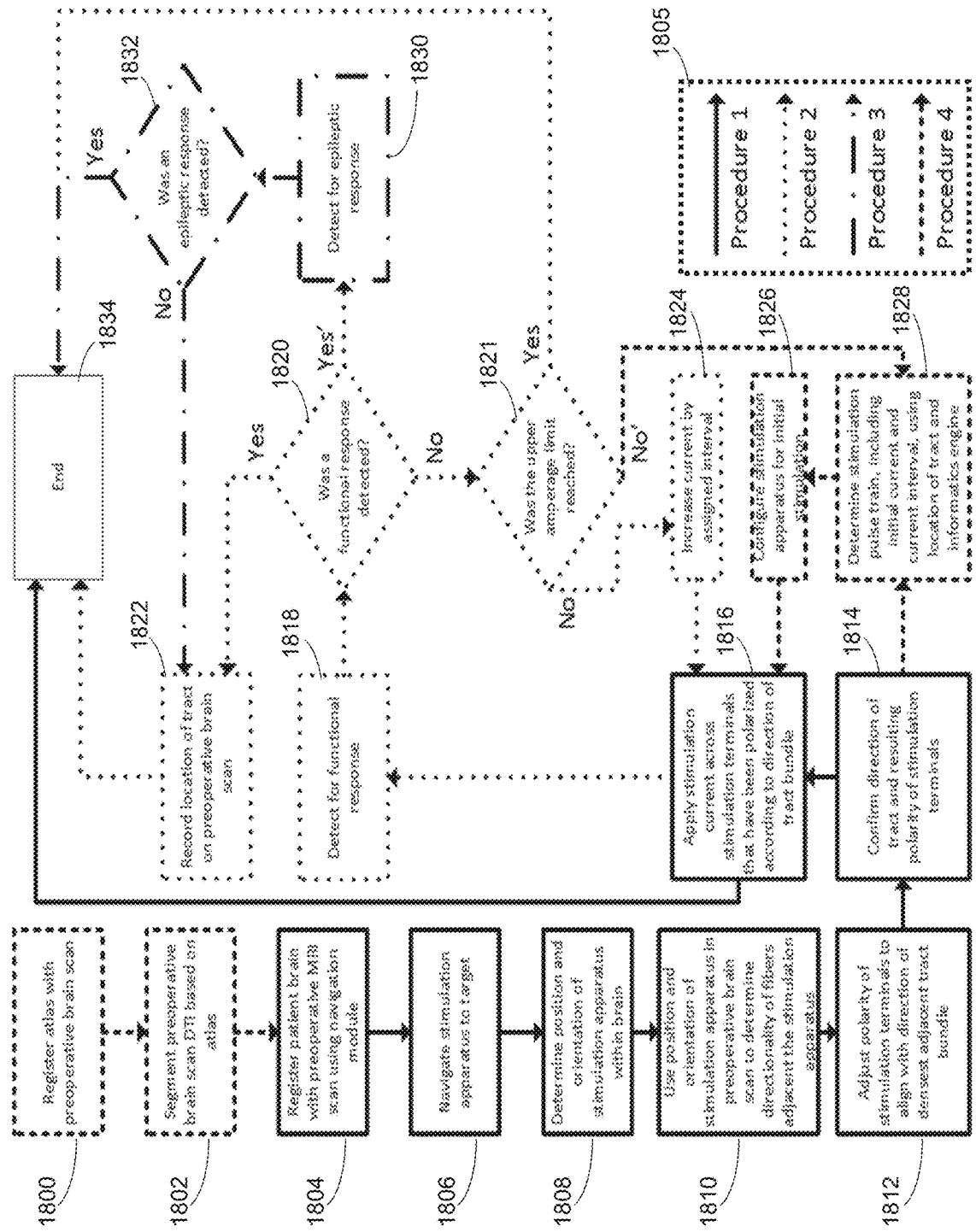
FIG. 18 Illustrates a flow chart describing multiple procedures that may be implemented using various stimulation systems.

FIG. 18 depicts a flow chart for procedures that involve the use of the stimulation system 1601 further enhanced with independent proponents of alternate surgical systems. Each of the procedures (Procedure 1 to Procedure 4) as outlined by the legend 1805 of the diagram involve the implementation of different embodiments of a functional stimulation system as disclosed herein, the functional stimulation system being formed of the stimulation system 1601 enhanced with additional independent surgical systems. Some examples of independent surgical systems include a navigation module inclusive of a tracking system and tools as described in patent application WO2014/139022—SYSTEMS AND METHODS FOR NAVIGATION AND SIMULATION OF MINIMALLY INVASIVE THERAPY, an imaging data module as outlined in patent application WO2014/139024—PLANNING, NAVIGATION, AND SIMULATION SYSTEMS AND METHODS FOR MINIMALLY INVASIVE THERAPY, an informatics engine such as outlined in patent application CA2014/050873—SYSTEM AND METHOD FOR HEALTH IMAGING INFORMATICS, an image data segmentation module as outlined in patent application CA2014/000740—SYSTEM AND METHOD FOR CONNECTIVITY MAPPING, an automated alignment system as outlined in patent application WO2014/139023—INTELLIGENT POSITIONING SYSTEMS AND METHODS THEREFORE, wherein all these patent applications are incorporated in their entirety herein by reference.

Procedure 1 as outlined in FIG. 18 may be performed using the stimulation system 1601 enhanced with a navigation module. An exemplary embodiment of such a stimulation system enhanced with such a proponent is shown in block diagram form as 1901 in FIG. 19. The navigation system enhancement of this stimulation system 1901 includes the addition of: a navigation module including a navigation processor integrated with the stimulation system processor 1900 for controlling the system; a preoperative data acquisition proponent 1905 for accepting or acquiring preoperative data; a tracking system 1910 for tracking surgical instruments (such as an embodiment of the apparatus 1635 as disclosed herein); stimulation tracking markers 1920 to enable tracking of such instruments; and a registration protocol for registering a patient with their preoperative data in image space 1915. In some cases the stimulation system may also be enhanced with EMG sensors affixed to the patient to add further efficiency to a functional stimulation procedure when performed using the embodiment of the stimulation system 1901 as described herein.

To elucidate further on the navigation module, an example of a surgical system enhanced with such a navigation module is provided in FIG. 1 illustrating navigation processor 101, tracking system 113, tracking markers 267, and a medical instrument in the form of a tracked access port 100. The procedure being performed in this case is a port type neurosurgery where the surgeon 103 is performing surgery in the brain of the patient 106 through the access port 100. The brain of the patient 106 in the operating theater as shown in the figure, has been registered with their preoperative brain scan relative to a patient reference marker 145 tracked by the tracking system 113 using a touch point registration as is known in the art. This allows the surgeon to utilize the patient's registered preoperative scans in combination with their tracked tools to guide their surgical intervention. A visualization of the preoperative scan relative to the surgeon's tracked tools is displayed on the surgical system display 111.

Procedure 1 generally describes a method to identify the optimal direction in which to stimulate a bundle of white matter tracts in the brain with a stimulation apparatus using preoperative imaging, followed by the application of a stimulation current to said white matter tracts. In order to identify the direction of a tract using the preoperative imaging of the patient, the orientation of the stimulation apparatus stimulation terminals (such as those disclosed herein) relative to the tractography of the patient must be known in physical space. One way to achieve that is to track the stimulation apparatus (medical instrument) relative to the patient in physical space during the surgery using the patient registered preoperative imaging (with corresponding coordinates in an image space) to identify the position and orientation of tractography in the patient's brain relative to the stimulation apparatus and inherently its stimulation terminals.

Figure 20:
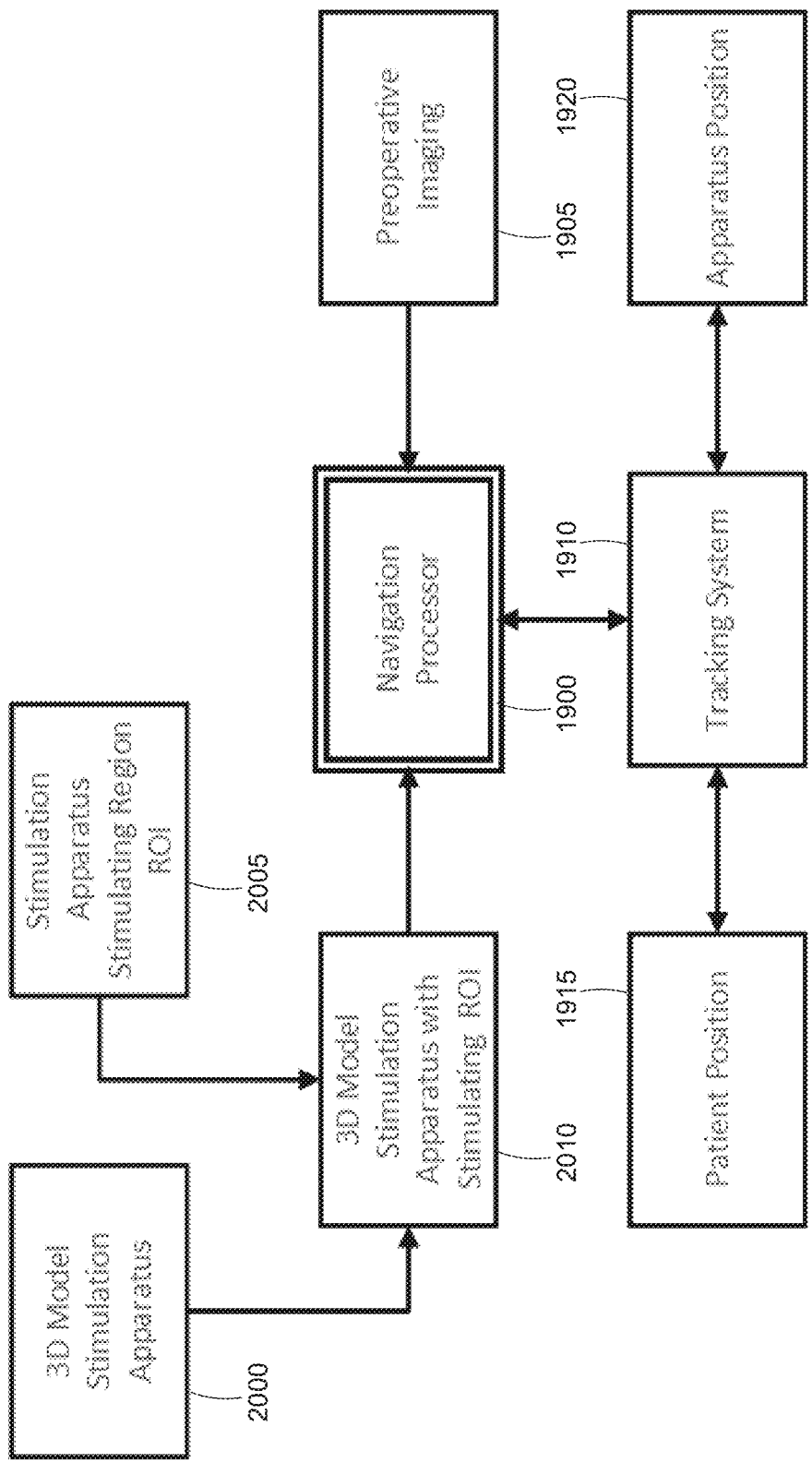
FIG. 20 Illustrates a block diagram showing exemplary inputs into a navigation system.

FIG. 20 is a block diagram showing some exemplary navigation processor inputs to further clarify the execution of Procedure 1 as per the flow chart depicted in FIG. 18, using the stimulation system 1901, and described in further detail below.

Figures 21A, 21B:
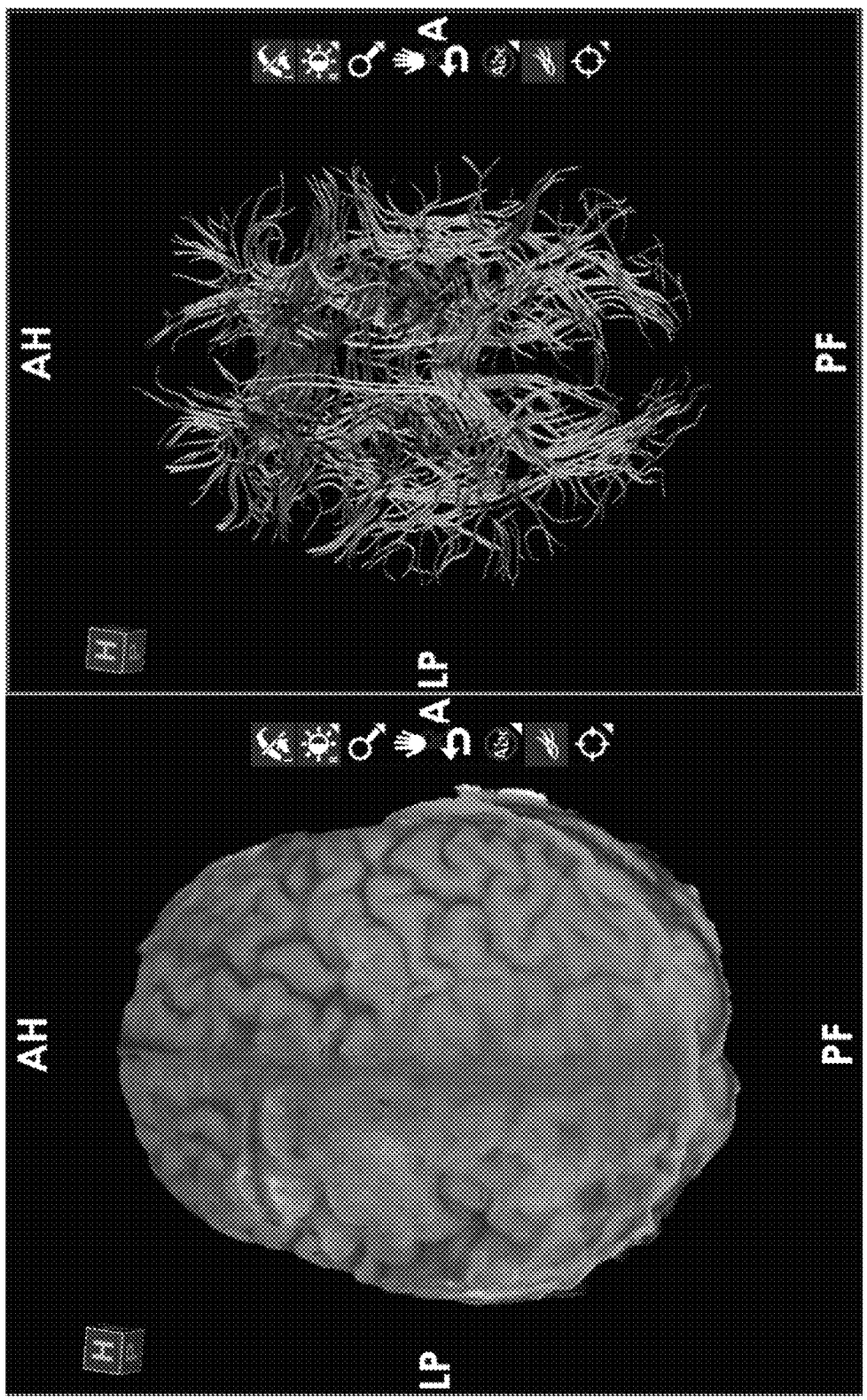
FIG. 21A and FIG. 21B Illustrates typical patient imaging taken from a neurosurgery planning platform depicting 3D views of a brain scan one showing the surface of the brain and the other showing the internal tractography.
Figure 22:
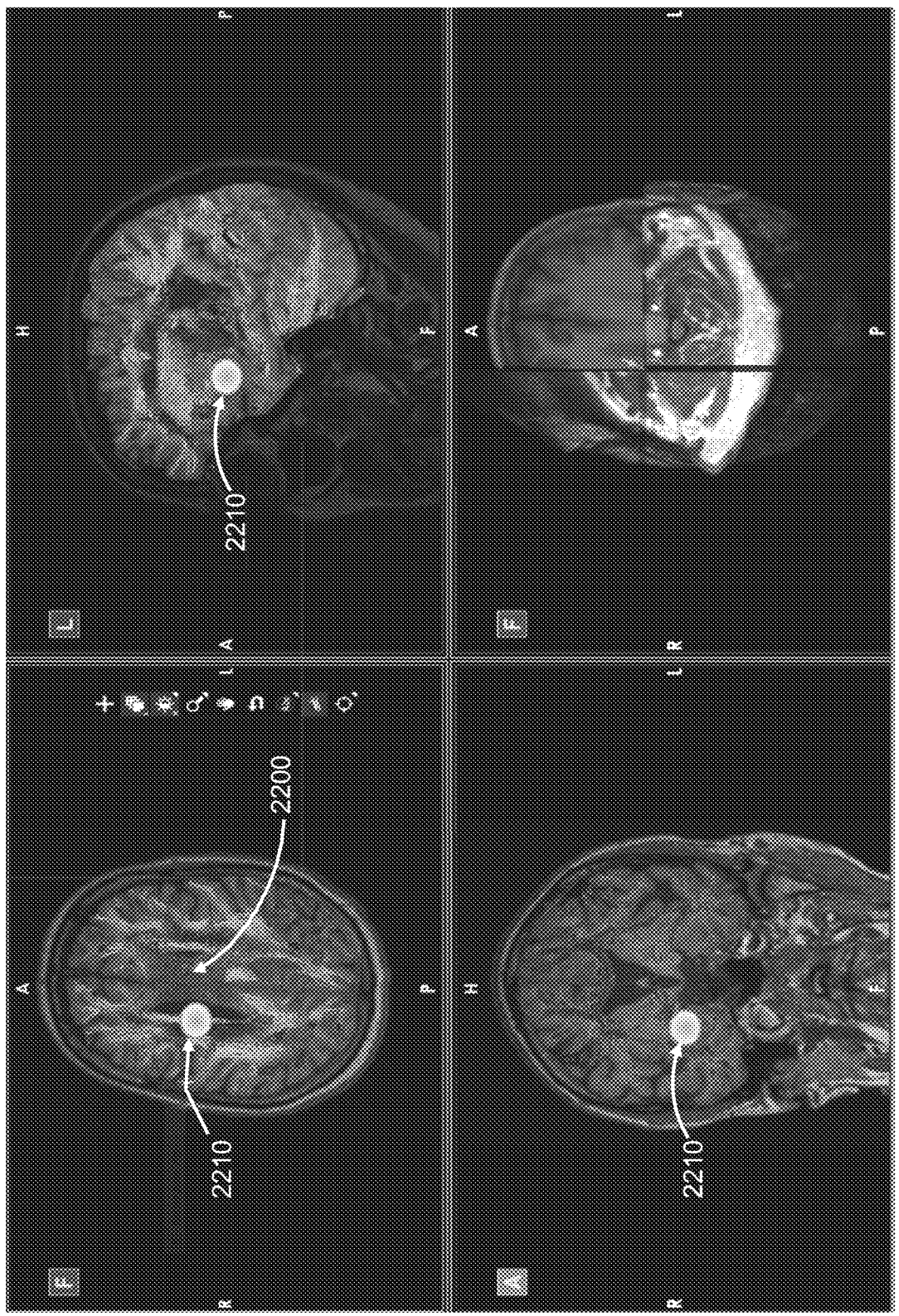
FIG. 22 Illustrates the typical patient imaging taken from a neurosurgery planning platform showing orthogonal slices of the brain.

FIGS. 21 and 22 show an exemplary preoperative imaging of a patient's brain including tractography information which may be input into the navigation processor 1900. The left frame 2100 of FIG. 21A shows the brain surface and structure while the right frame 2105 of FIG. 21B depicts the internal tractography of the same from an identical viewing angle. FIG. 22 depicts three cross sectional stacked views in the sagittal, coronal, and axial viewing angles of a patient's preoperative imaging, where the T1 type MM images are overlaid with the corresponding tractography. The inferior segment of the corona radiata may be seen at 2200 in the image by its representative tractography. When registered with the patient using a navigation system such as the system shown in FIG. 1 the preoperative images and resulting clinical information of the patient will correspond to the patient in physical space and its position and orientation will therefore also be known relative to the position and orientation of the stimulation apparatus. Thus in order to facilitate the execution of Procedure 1 as described above both the preoperative MIll tractography 1905 and patient position in physical space 1915 (via the tracking system 1910) should be inputted into the navigation processor 1900 as shown in FIG. 20.

To identify the position and orientations of the stimulation terminals relative to the patient and their spatially registered preoperative scan, a 3D model of the terminals defined relative to a set of tracking markers and attached to the apparatus may be employed. This 3D model may then be input into the navigation processor 1900 as shown in FIG. 20. The 3D model may include one or more Regions of Interest (ROIs) defined relative to the apparatus, and inherently the stimulation terminals, that define one or more regions where a stimulation current may be applied. For example, as shown in FIG. 23 the stimulation ECoG port apparatus 1001 may be tracked by attaching a tracking marker arrangement 2305 having tracking markers 267 and further having an ROI 2300 representing a volume in a defined position and orientation relative to the tracking markers 267. This volume 2300 represents a region through which a stimulation current may be applied using the stimulation terminals of the stimulation apparatus. In general the ROI may be integrated into a 3D model of the apparatus, where the apparatus has a known position and orientation in image space as derived from its tracking arrangements' position and orientation in physical space, as is commonly implemented in the art. As a result of such an integration, the ROI volumes position and orientation may also be determined relative to the spatially registered patient imaging in the image space. Thus to facilitate the execution of Procedure 1, a 3D model of the stimulation apparatus 2000 integrated (2010) with a corresponding ROI 2005 identifying a volume wherein a stimulation current may be applied, the stimulation, and the position of the apparatus 1920 should be inputted into the navigation processor 1900.

To further elaborate on the mentioned 3D model including its ROI, FIG. 24A depicts an exemplary navigation system view 2430 of a 3D model of a real-time tracked stimulation port apparatus 2400 within a brain region 2410, in 3D view 2440 as well as brain striped view 2450. As is apparent from the image, the ROI 2405 defined relative to the port apparatus' position and orientation is visible. As is described above this ROI may be used to determine the white matter tracts that may be stimulated by the stimulation apparatus. This is apparent from FIG. 24B where the tractography of the patient imaging 2420 which passes through the ROI volumes 2405 are shown in the middle 2440 and right 2450 frames of the figure. It should be noted that the tracts that pass through the volume change as the port is manipulated. This effect is illustrated as the difference in tracts shown between the highlighted tractography 2420 in the middle frame 2440 and right frame 2450 in FIG. 24B and FIG. 24C. As the port apparatus is manipulated this ROI moves accordingly such that it is in a statically defined position and orientation relative to the port itself, which may again be apparent from the differences in highlighted tractography shown in the middle and right frames of FIG. 24C. Defining such an ROI can be done at different scales, shapes, and orientations relative to a medical instrument such as a tracked stimulation port 2400 as shown in FIG. 24C. The stimulation system 1901 may employ this same ROI implementation to determine upon which tracts a stimulation may be applied. Further examples of defining ROI's are described in international patent publication No. WO 2014/139024, titled "PLANNING, NAVIGATION AND SIMULATION SYSTEMS AND METHODS FOR MINIMALLY INVASIVE THERAPY", the contents which is incorporated by reference herein.

Figure 25B:
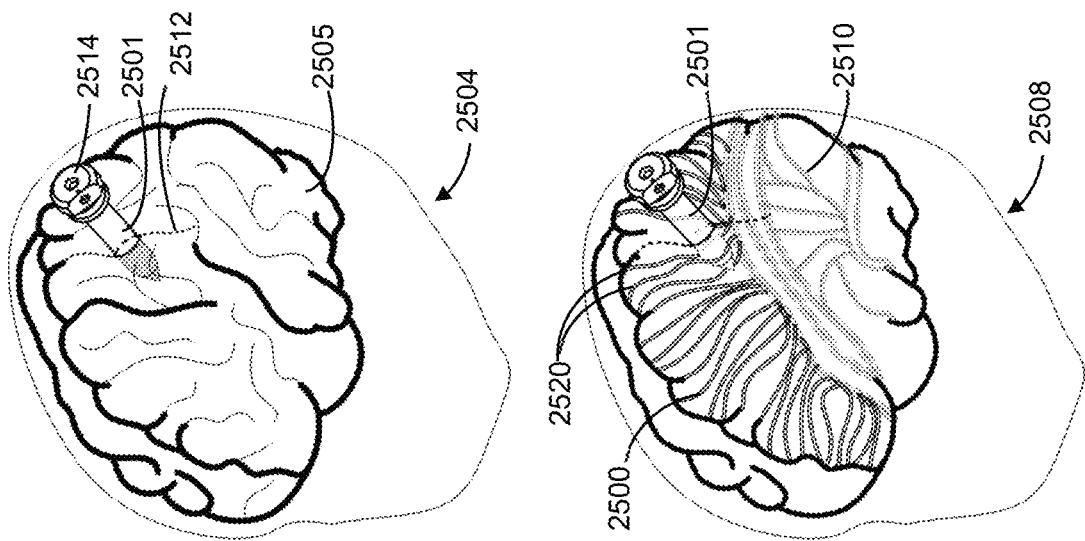
FIG. 25A and FIG. 25B Illustrates the two different views of two different stages of a port based neurosurgical procedure.
Figure 25A:
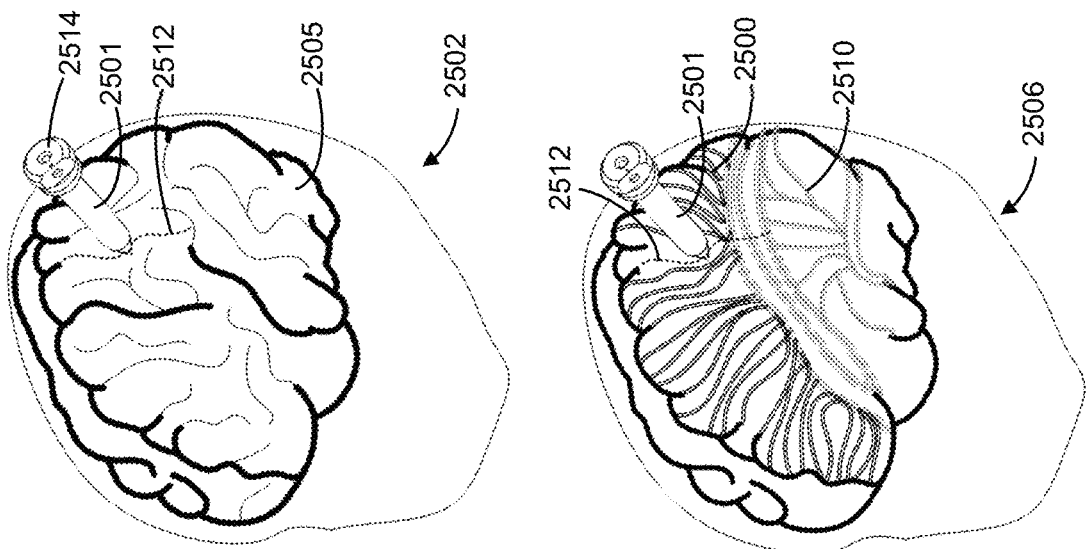
Figure 26:
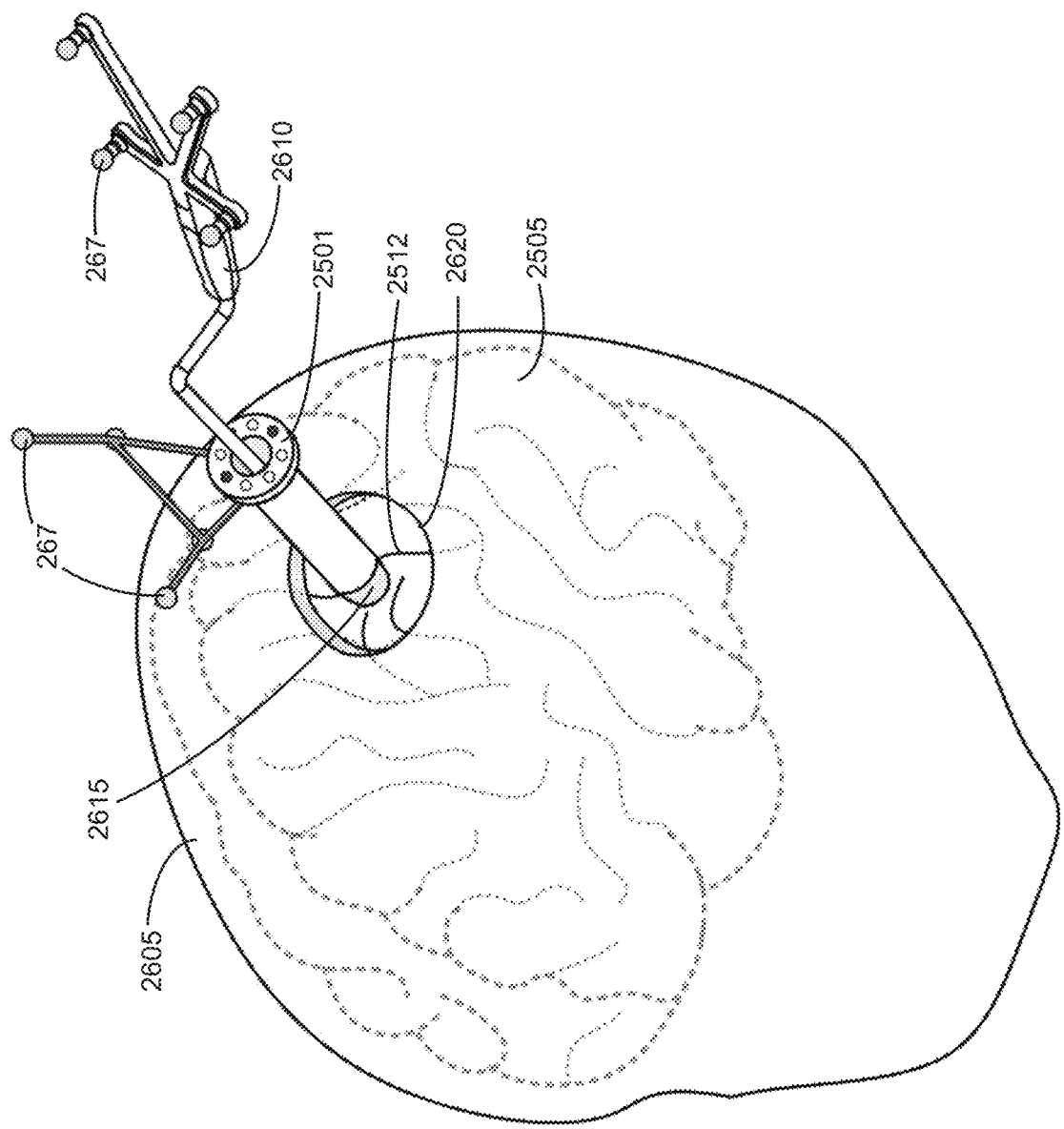
FIG. 26 Illustrates the use of the tracked stimulation ECoG port apparatus and a medical instrument during a port based medical procedure.

FIG. 25A and FIG. 25B depicts two stages of a port based neurosurgical procedure as described above. The top left frame 2502 of the figure is a diagram showing a neurosurgical procedure before an access conduit 2501 has been inserted into a subsurface region of the brain 2505 through a sulcus 2512 and a layer of skull (not shown). The lower left frame 2506 shows the same stage with the tractography of the brain showing, such as that derived from a DTI MM scan, an example of which is shown in the right frame 2105 of FIG. 21B. The tractography shown in the diagram 2506 is specifically representative of the white matter tracts in the anatomical regions of the brain 2505 corresponding to the Corona Radiata 2500 and the Corpus Collosum 2510. Although in some cases these tracts may not be identified as such and may just be generic white matter tractography, such as shown in 2105, the surgeon may in such cases identify the tracts using their experience. It should be noted that these anatomical tractography regions were segmented out of the surrounding brain tissue for illustrative purposes only. The top right diagram 2504 shows the second stage of the neurosurgical procedure where the access conduit 2501 has been advanced to a target (not shown) in the brain 2505 through the sulcus 2512 and a layer of skull (not shown). As is apparent from the image, the access port has penetrated the brain's outer surface providing a corridor through which a surgeon may access the target area (not shown) after removal of the obturator 2514 (used for cannulating the port to the target area), such as shown in FIG. 26. Referring back to FIG. 25B once again the bottom right diagram 2508 of the figure shows the same stage of the surgery as the diagram 2504 but instead of the brain it shows the tractography of the patient. As is apparent from this diagram the access conduit 2501 is in contact with two tracts 2520 of the Corona Radiata 2500. Thus if an embodiment of the stimulation port apparatus as disclosed herein, for example stimulation port apparatus 401 or apparatus 1001, were to be used in place of the access port 100 the surgeon would be able to stimulate these tracts.

FIG. 26 shows a third stage of a port based neurosurgical procedure as described above with additional elements not shown in the preceding two stages. In this image the surgeon (not shown) is performing surgery on the target area (not shown) in the brain 2505 using medical instrument 2610. Access to the target region was attained by advancing the access conduit 2501 with obturator 2514 through the skull 2605 via a craniotomy 2620 and further through a sulcal fold 2512 in the brain 2505 and removing the obturator after the target is reached. It should be noted that both the access conduit and medical instrument may be tracked by a tracking system (such as 1910) using tracking markers 267 in the manner described above.

When performing this third stage of the surgery a surgeon commonly uses a navigation module to track the location of the medical instrument 2610 relative to the brain 2505 of the patient according to a registered preoperative brain scan (such as that depicted in FIG. 22). An example view of what a navigation module may display to a surgeon (such as via display 111 in FIG. 1) is provided in FIG. 24A, FIG. 24B and FIG. 24C where an access conduit 2400 is shown relative to a brain scan 2410 of a patient in image space. The position and orientation of the visualized access conduit 2400 relative to the patient's registered preoperative brain scan 2410 in image space is more or less proportionally equivalent (with respect to a spatial coordinate space), to the position and orientation of the tracked access conduit (such as 2501) relative to the patient's brain 2505 in physical space as is known in the art. This view provided by the navigation system assists in guiding a surgeon by showing them a preoperative image of a location in the patient's brain, where their surgical instrument is presently located and where their view may be occluded by the patient's skull or opaque brain matter. Thus a surgeon may use preoperative imaging of a patient to guide them in maneuvers performed within a patient's brain from viewing angles where their view may be occluded by a patient's skull or opaque brain matter.

Figure 19:
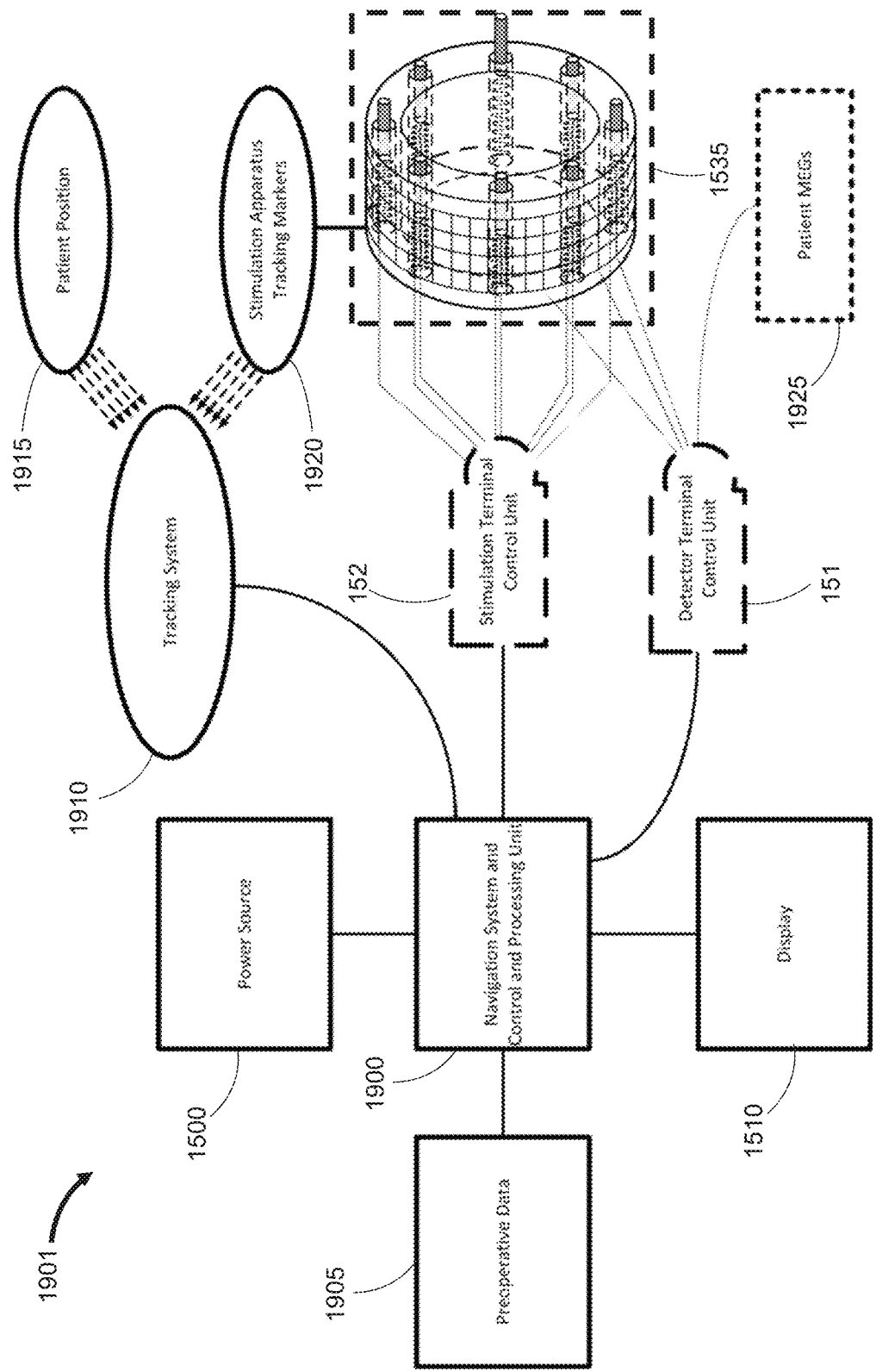
FIG. 19 Illustrates a block diagram of a generic stimulation system which may or may not employ the stimulation ECoG port apparatus enhanced with a navigation module.
Figure 27:
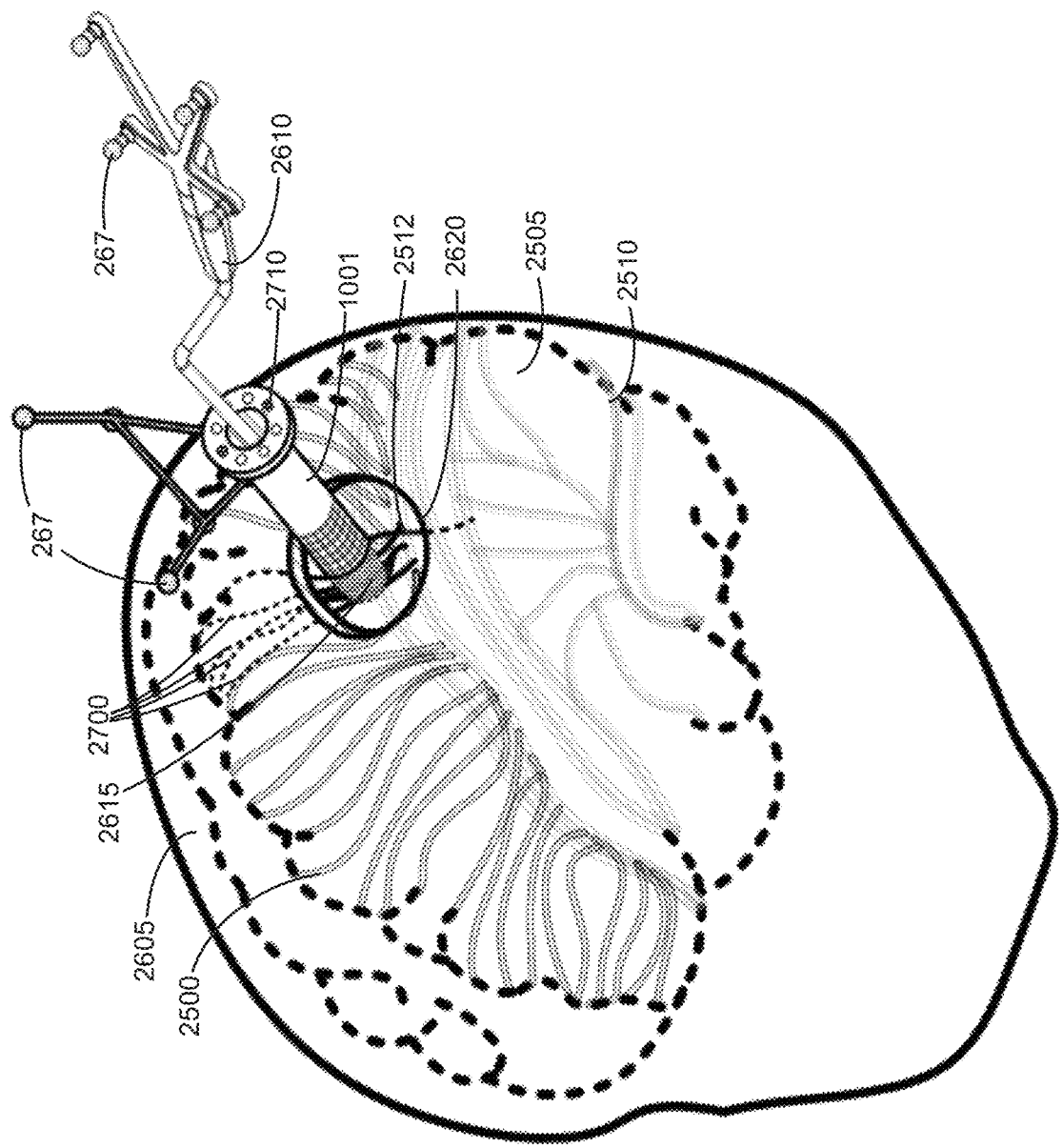
FIG. 27 Illustrates an alternate view of the use of the tracked stimulation ECoG port apparatus and a medical instrument during a port based medical procedure.

Referring back to Procedure 1 shown in FIG. 18 the first step 1804 in the procedure is to register the patient to their preoperative brain scan such as shown in FIG. 1, using the navigation module and more specifically the tracking system 1910 as described above in further detail and as is known in the art. This registration information may then be provided to the navigation system and control and processing system 1900 as shown in FIG. 19 and described in further detail above. The next step 1806 in the process is to navigate to the target using a stimulation apparatus such as the stimulation ECoG port apparatus 1001 or an equivalent device. Following the arrival of the stimulation apparatus to the target the next step in the procedure is to acquire the position and orientation of the stimulation apparatus (Apparatus Position 1920) relative to the registered preoperative scan in image space, which may be accomplished using the tracking system 1910 and the stimulation apparatus tracking markers 1920. This information (Apparatus Position 1920) may then be inputted into the Navigation System and Control Processing unit 1900. In the following step 1910 the Navigation System and Control and Processing Unit may be programmed with instructions to use the pre-inputted ROI information from the 3D Model Stimulation Apparatus with Stimulating ROI 2010, the Apparatus Position 1920, and the position of the patients registered tractography derived from the Preoperative Imaging 1905 of the patient to compute the optimal direction to apply a stimulation current to the tracts adjacent the stimulation apparatus. For example, FIG. 27 shows the same stage of a surgery as FIG. 26 but the preoperative imaging is rendered in a tractography form without the surrounding solid brain mass tissue. The diagram in this figure is representative of potential information inputted into the Navigation System and Control and Processing Unit and the physical orientation of objects in the operating space. From this diagram it is apparent that the distal end of the stimulation ECoG port apparatus 1001 is positioned adjacently to white matter fiber tracts of the Corpus Collosum 2500. The ROI region 2615 of the apparatus shows the overlap of tracts and the volume in which a stimulation current may be applied by the tracked apparatus 1001. It is apparent that the particular tracts 2700 of the Corpus Collosum that may be stimulated overlap with ROI volume 2615 of the port 1001. Thus, the Navigation System and Control and Processing Unit 1900 may determine the segments of these fiber tracts 2800 located in the volume and further analyze their relative (to the apparatus' 1001 orientation) directionality to determine their optimal stimulation current direction. The directionality of these tracts may be determined by processing the image data in the region 2615 relative to the orientation of the apparatus 1001 and applying known computational methods as discussed in international publication WO 2014/138997, titled "SYSTEM AND METHOD FOR DETECTING TISSUE AND FIBER TRACT DEFORMATION" where the contents are incorporated by reference herein. Once the directionality is determined the process may proceed to the next step 1812. The Navigation and Control and Processing Unit 1900 may adjust the polarity of stimulation terminals by assigning a pair of terminals as positively and negatively polarized, such as 1500 shown in FIG. 15, situated on the distal end of the apparatus adjacent the tracts. The relative direction of the polarity of the stimulation terminals may be displayed to the surgeon using a display such as 1610 and also displayed on the port by illuminating the directional indication LED's 2710 as described in further detail above. As per the following step 1814 the surgeon may then address the Navigation System and Control and Processing Unit via the display 1610 to confirm or reject the assigned stimulation terminal polarity. Once confirmed the final step 1816 of this procedure may be executed where the stimulation terminals assigned the polarities are used to apply a stimulation current to the adjacent tractography. It should be noted that the use of the stimulation apparatus 1001 as described above is not to be taken as limiting the scope of the procedure as described herein and variants of the apparatus may be employed when performing Procedure 1 as described above. For example, bipolar stimulation probe 300 may be employed in a similar manner to that of the apparatus where the ROIs of the apparatus would be defined as the area directly adjacent the prongs 304 of the probe.

Use of Probe with Navigation System for Recording Location of Successful Stimulation In further embodiments of the stimulation system 1901 as disclosed herein the clinical results of a stimulation application (for example successful stimulation, epileptic stimulation, null) may be mapped to the position where that stimulation was applied in the patient's brain (or in some embodiments other tissues such as the spine). This can be achieved by using the tracking system to link the position of the stimulation apparatus with the preoperative imaging of the patient (or in some cases the intraoperative imaging) in image space, thereby allowing the system to place a positional marker (point, volume, or such) associated with the data at that position. For example if when stimulating an area in the motor cortex a motor response is detected in the patient (for example loss of hand functionality) the point(s) where the stimulation was applied (and potentially the direction of stimulation) may be recorded on the patient imaging and associated with the results. More specifically a surgeon may be able to reference that point again (for example through the use of a display such as 1610 shown in FIG. 19, and a surgical system such as BrightMatter Guide™ produced by Synaptive Medical Incorporated) and acquire knowledge about the stimulation that was applied at that point, such as whether the stimulation was successful and the amount of voltage applied across the terminals to induce a functional response in the patient. This may be accomplished by employing software that allows targets to be placed on patient imaging such as by the software mentioned above and disclosed in patent application WO2014/139022—SYSTEMS AND METHODS FOR NAVIGATION AND SIMULATION OF MINIMALLY INVASIVE THERAPY, as well as, WO2014/139024—PLANNING, NAVIGATION, AND SIMULATION SYSTEMS AND METHODS FOR MINIMALLY INVASIVE THERAPY, the contents which are herein incorporated by reference. It should be noted that the target (point or volume) in this case may be placed automatically by the software as per the position and orientation of the ROI defined relative to a stimulation apparatus used to apply said stimulation current. An example of such a positional marker is shown as 2210 in FIGS. 22 and 24. In FIG. 24A the positional marker 2210 is shown on an exemplary navigation interface that may be displayed by the stimulation system while a surgeon is performing surgery. The surgeon may access the corresponding information related to the positional marker by performing an action on the interface such as scrolling over the point with their mouse, or selecting it using a drop down list, or by any other applicable means implementable on navigation GUI (graphical user interface) as is known in the art. It should be noted that the point may be formed at the position of stimulation according to the ROI position 2210 such as shown adjacent to the stimulation port 2400 in FIG. 24A.

As described above, during a cortical mapping and/or functional stimulation procedure it is common for a surgeon to apply multiple stimulation currents to the same white matter tract to try and elicit a functional response from the patient. This repetitive process is generally iterative wherein the surgeon will consecutively increase the stimulation current in a pre-determined range from a lower limit to an upper limit. An example is described in Bello, Lorenzo, et al. "Combined Use of DES, EMG and MEP Monitoring, ECoG and EEG for Surgical Resection of Gliomas." (2008): 72-74. This iterative process is performed in order to minimize potential trauma to the patient caused by electrical damage and induced epileptic seizures. Generally when a surgeon is stimulating a white matter tract they will begin with a low current such as 2 mA as outlined in the above cited paper and increase this current by a given interval such as 0.5 mA, also outlined in the above cited paper, until they detect a functional response in the patient. For example if a surgeon is performing surgery in or around the language cortex of the brain they will perform a stimulation and ask the patient to say something in order to verify if the stimulation is affecting their speech (function). If the patient can speak properly they will iteratively repeat this process of stimulation and verification increasing the amperage of the stimulation at the given interval during each iteration, until they reach an upper amperage threshold at which point they would stop increasing. If the upper threshold is reached with no functional response detected (verified) they may pragmatically conclude that the tract is unrelated to the language function of the patient and may in some procedures resect that area. However in some cases the application of a stimulation current may result in the patient having an electrically induced epileptic seizure (epileptic response). If this occurs the patient's function being tested (verified) may very well be affected, for example the patient's speech ability may suffer. However this reduction in speech function cannot be verified as a direct result of the tract being stimulated due to the unconstrained neuronal firing caused by the epileptic response. Thus, the verification of the effect on the functional response of the patient in this case would be voided as a true indicator of the function of the tract which was stimulated. In addition when an epileptic response is induced at a certain functional application amperage the surgeon may determine this amperage to be an upper limit threshold. Since increasing the stimulation current past the initial current that caused such an epileptic response is likely to result in further epileptic response, providing no additional opportunity to verify the function of the tract and potentially causing at the very least a traumatic experience to the patient and at the very most electrically induced brain damage.

As described above epileptic responses to stimulation may generally be determined during the surgery through the employment of ECoG sensors. These sensors will aid in invalidating false positives by identifying the cause of a functional response of a patient, potentially resulting from a stimulation induced epileptic seizure as opposed to a directed stimulation application. Again this process may be performed by an ECoG access conduit as described above or the stimulation ECoG port apparatus. It should be noted that, although not ideal, the iterative stimulation process described above may be performed without testing for epileptic responses and may consist of increasing the stimulation current by the given interval at each iteration from the lower limit to the upper limit.

Figure 28:
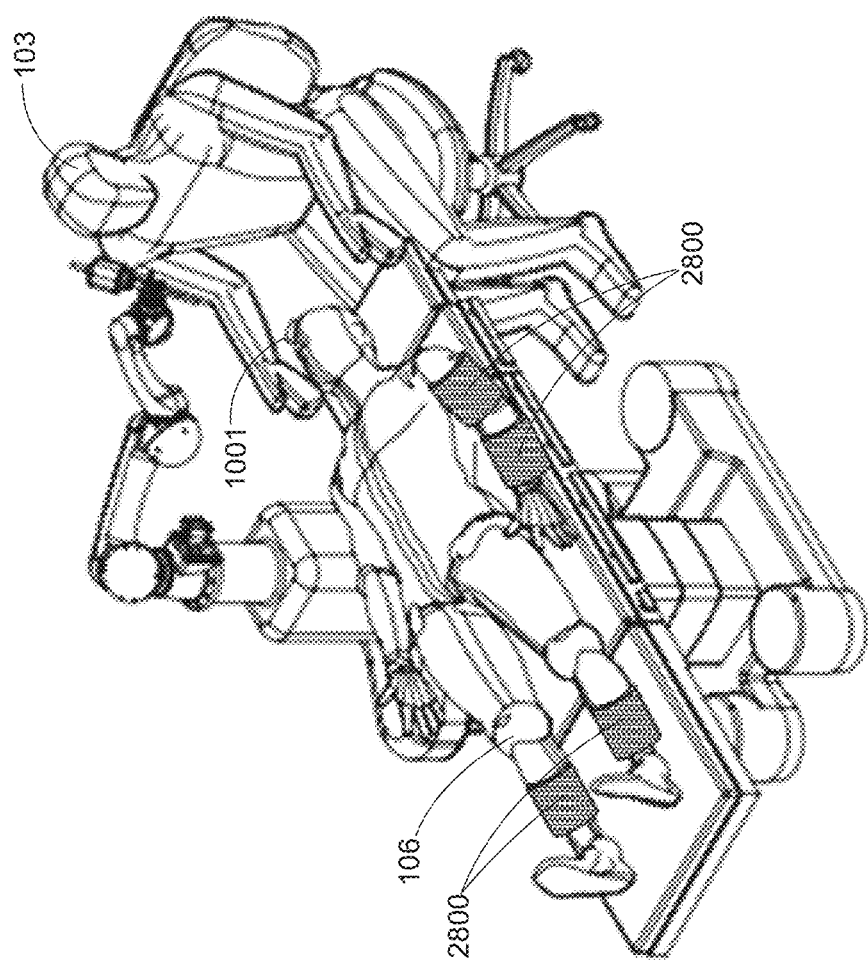
FIG. 28 Illustrates the use EMG sensors on a patient during a neurosurgical procedure employing the tracked stimulation ECoG port apparatus as part of a stimulation system.

The process of acquiring stimulation information about a tract as per the iterative stimulation process described above and then mapping the position of this stimulation information to patient imaging is reflected by Procedure 2 shown in the flow chart in FIG. 18. This embodiment of the procedure is an extension of Procedure 1 and may be performed with the stimulation system 1901 depicted in FIG. 19. This extension introduces both an iterative loop (1818→1824), as well as a step 1822 to map the information acquired from the stimulation application to the patient imaging. Procedure 2 deviates from Procedure 1 after a stimulation current is applied at step 1816. Following the application of this stimulation current in step 1816 the procedure enters a first iterative stimulation loop. The first step 1818 in the loop following the application of a stimulation current in the previous step 1816 is to detect (verify) for a functional response by the patient. This step may comprise of a neurologist verifying a response of a patient in performing a task involving the suspected function of the tract being stimulated. Again this may take the form of the neurologist verifying the ability of the patient to speak when the function of the tract is suspected to be related to the speech cortex of the brain, or in an alternate example, the neurologist may check the eyesight of the patient if the tract is suspected to be related to optical function of the patient. In some embodiments where a surgeon is operating in or around the motor cortex of the brain, this step may be performed by sensors such as EMGs placed on the surface of the patient's skin and connected with a stimulation system such as EMG sensors 1925 connected to system 1901 shown in FIG. 19. EMG sensors may be used to detect nerve stimulation in muscle tissue. Thus placing them over important areas such as the arms, legs, or hands during cortical stimulation of the brain tissue that controls the muscles of these areas may allow a surgeon to more quantitatively detect a functional stimulation response of a patient and provide a more beneficial outcome. Accordingly these patient EMG's may be integrated directly into the stimulation system being employed to apply the stimulation current. For example as shown in FIG. 19, the patient EMGs 1925 are inputted into the detector control unit 1615 which is in turn inputted directly into the Navigation System and Control and processing unit 1900 allowing any stimulation response information acquired from the patient EMGs to be inputted directly into the processor. An exemplary view of a stimulation procedure employing EMG sensors 2800 is shown in FIG. 28. In the figure the surgeon 103 is performing a stimulation procedure on the patient 106 through the stimulation ECoG port apparatus 1001. Moving forward as per Procedure 2 the next step 1820 in the loop is a decision step of whether a functional response was detected. If a functional response was not detected, the loop continues and proceeds to another decision step 1821 where the previously applied amperage is checked against a predetermined upper limit as described above to determine whether the functional stimulation of the tract should be halted. If the upper limit is reached the process proceeds to step 1834 ending the stimulation application. However if the limit is not reached the process continues the loop and proceeds to the following step 1824 where the current amperage is increased by the given interval, after which the process continues to step 1816 as described above to restart the loop. If a functional response is detected at step 1820 the process then alternately proceeds to step 1822 where the functional stimulation application information is recorded about a positional marker at the position where the stimulation current was applied on the patient imaging such as the positional marker 2210 shown in FIGS. 22 and 24. Once the step 1822 is completed procedure 2 advances to the last step 1834 where the process ends. It should be noted that in step 1822 the positional marker may include an indicator to communicate the direction of the current which was applied and the stimulation application information may include information from every stimulation that was applied each time the loop 1816→1818→1820→1821→1824→1816 was completed. Again this information may comprise data such as the current amperage, the frequency of the current application, the direction of the current application, the resistance of the tract to the current application, etc. In some embodiments the information recorded may be any of the parameters including frequency, voltage, sampling rate, amperage, waveform, polarity, lower limit and sensitivity. It should be noted that the parameters frequency, voltage, sampling rate, amperage, waveform, polarity, lower limit and sensitivity, may also in some cases be ECoG sensor parameters, and although not described in the embodiment of the execution of Procedure 2 shown in FIG. 18, these parameters may be employed as per the execution of Procedure 3 described below. Thus any information acquired by the ECoG sensors and the particular parameters used for those acquisitions may also be recorded in addition to the stimulation information in correspondence with the position of the applied stimulation current via the positional marker.

Procedure 3 as shown in the flow chart depicted in FIG. 18 reflects a similar process to that of Procedure 2 but in addition to employing the stimulation apparatus it also employs an ECoG grid, which allows for the voidance of false positive stimulation responses that may have been caused by a stimulation induced epileptic response. This embodiment of the procedure shown in FIG. 18 is an extension of Procedure 2 as described above and may be performed with the ECoG sensors formed as part of the stimulation port apparatus 1635 in the stimulation system 1901 shown in FIG. 19. In the embodiment shown of the stimulation system 1901 the ECoG sensor grid in addition to the patient EMG's 1925 are integrated with the Navigation System and Control and Processing Unit 1620 via the Detector Terminal Control Unit 1615. It should be noted that both the Patient EMG's 1925 and the ECoG grid formed as part of the stimulation ECoG port apparatus 1635 and consequently the Detector Terminal Control Unit 1615 are optional additions to the stimulation system 1901 and may or may not be included in its implementation. Thus including or excluding these elements from the stimulation system 1901 depending on its use allows for the formation of additional embodiments. The addition and exclusion of these elements may be considered in light of the procedures as described herein. For example having these elements present is required when executing Procedure 3. Procedure 3 extends on the steps performed in procedure 2 with two additional steps that may be executed to determine and void false positive functional responses from the patient in the manners described above. The first step 1830 in this addition extends from step 1820 in Procedure 2 where if a functional response is detected the ECoG grid is activated to acquire a signal to determine if epileptic activity is detected within the patient's brain. Once a signal is acquired from the ECoG grid the procedure advances to the next step which takes the form of a decision step 1832 where the signal is analyzed (for example by the Navigation System and Control and Processing Unit 1900) to determine whether it correlates to an epileptic response. If the signal is found to correlate to such a response the procedure advances to the end step 1834 where it is terminated. If the signal is not found to correlate to an epileptic response the stimulation response detected is a true positive and thus the procedure advances back into Procedure 2 where the position of the successful stimulation is recoded at step 1822 as described in detail above. As it is apparent from the description of Procedure 3, the addition of the two steps to Procedure 2 may allow the employment of a stimulation system to determine when a false positive stimulation response is detected during a cortical mapping or stimulation assisted neurosurgical procedure.

Figure 29:
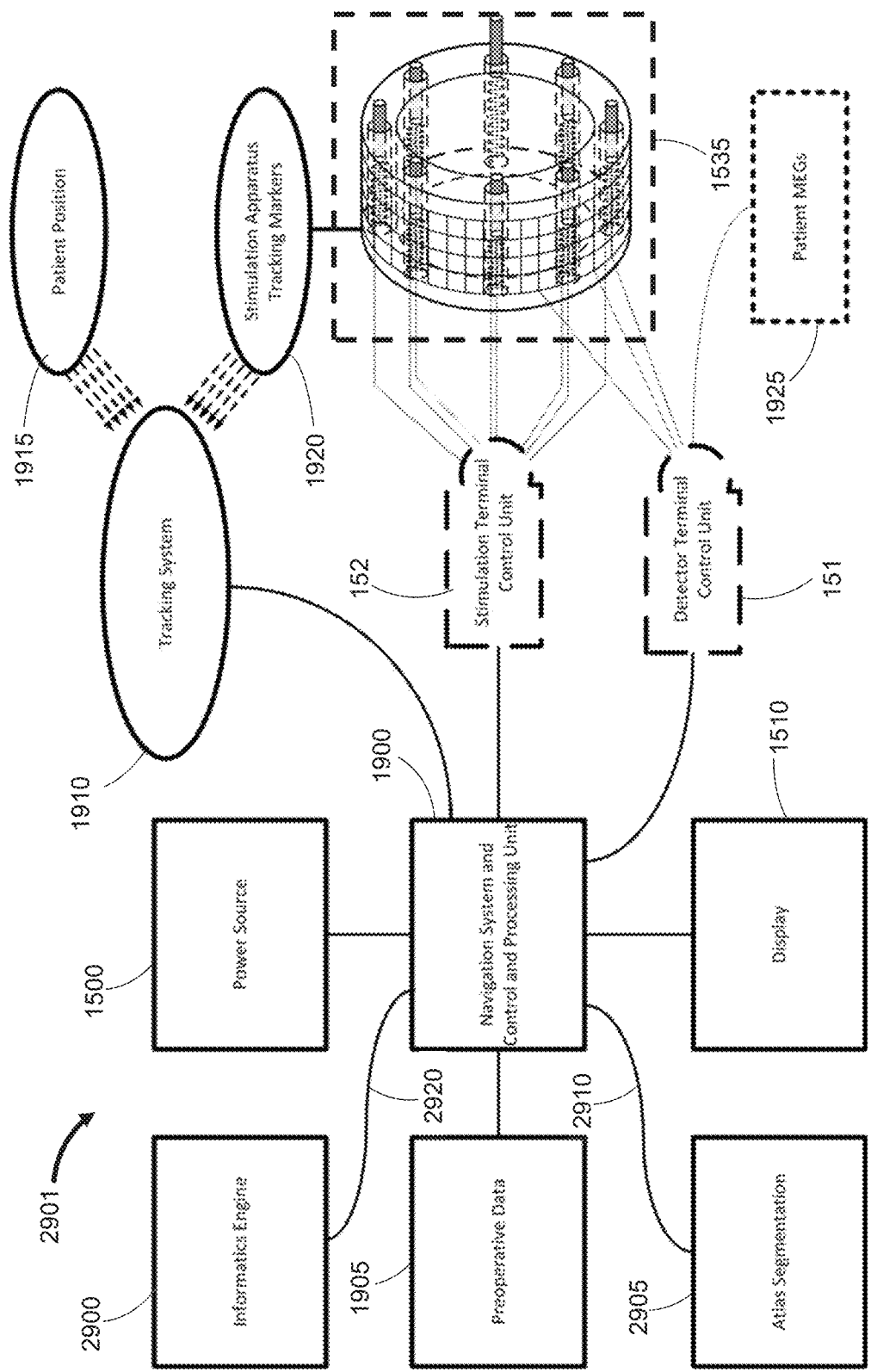
FIG. 29 Illustrates a block diagram of a generic stimulation system which may or may not employ the stimulation ECoG port apparatus enhanced with a navigation module and further enhanced with atlas segmentation and informatics engines.
Figure 31:
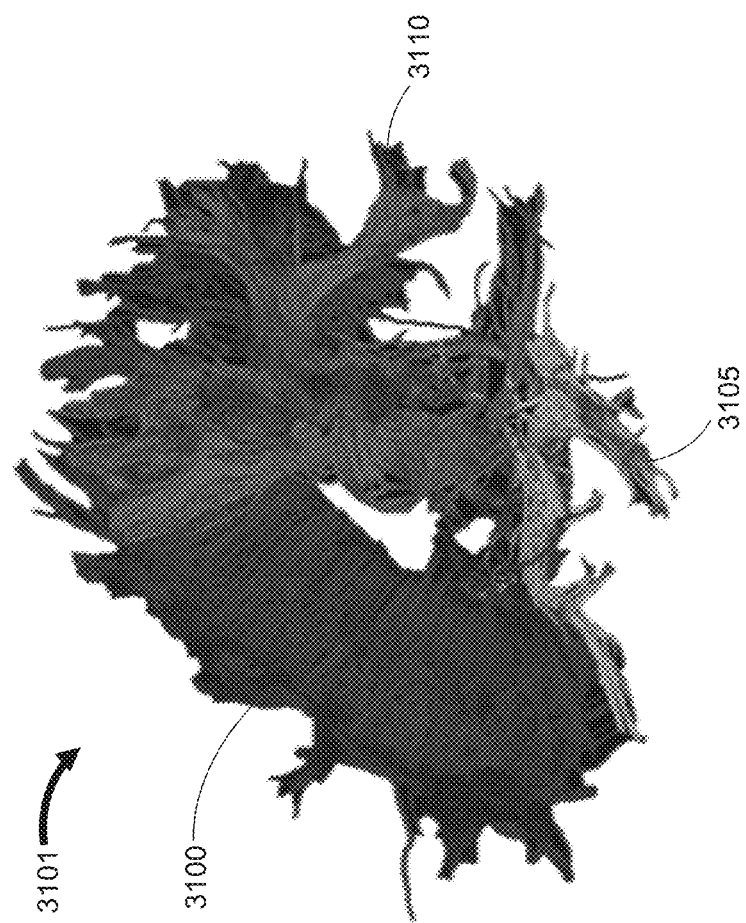
FIG. 31 Illustrates atlas segmented patient imaging.

Use of Probe with Navigation System, Tractography Segmentation, and Informatics Engine to Determine Correct Stimulation Pulse Procedure 4 as outlined in FIG. 18 may be performed using the stimulation system 1601 enhanced with a navigation module 1900 such as that shown as 1901 in FIG. 19 and further enhanced with atlas segmentation and informatics data shown as 2905 and 2900 in FIG. 29 respectively. An exemplary embodiment of such a stimulation system enhanced with such a proponent is shown in block diagram form as 2901 in FIG. 29. The enhancement of this stimulation system 2901 includes the addition of an atlas segmentation engine 2905, including a processor either integrated with the Navigation System and Control Processing Unit 1900 or having a separate integration component (such as 2910) for segmenting preoperative imaging of the patient and providing this information for use with the Navigation System and Control Processing Unit 1900. This imaging segmentation may be performed on MR data, CT data, or any other type of applicable imaging data and may be achieved according to a predetermined atlas using ROI's or some other form of segmentation in accordance with for example methods outlined by international patent application CA2014/000740—SYSTEM AND METHOD FOR CONNECTIVITY MAPPING, the content which are herein incorporated by reference. The second element used to enhance the stimulation system 2901 is the Informatics engine 2900 either integrated with the Navigation System and Control Processing Unit 1900 or having a separate integration component (such as 2920) for providing stimulation informatics to potentially improve the choice of stimulation parameters. The informatics engine may provide the surgeon with context specific information customized for the patient being operated on and the type of surgical operation being performed in addition to collecting surgical data for future stimulation assisted neurosurgical operations. The manner in which this information is provided may have many forms such as a ranking method provided in further detail below. It should be noted that both the described engines used to enhance the stimulation system 2901 may be employed independently from one another but are provided here as part of the same enhancement for exemplary purposes. In addition it should be noted that the preoperative data acquisition proponent 1905 for accepting or acquiring preoperative data may also be integrated with the informatics engine such that the preoperative imaging data provided to the Navigation System and Control Processing Unit 1900 is enhanced with fiber segmentation, an example of which is shown in FIG. 31 and elaborated on in further detail below. In some cases the stimulation system may also be enhanced with EMG sensors 1925 affixed to the patient to add further efficiency to a functional stimulation procedure when performed using the embodiment of the stimulation system 1901 as described herein.

Procedure 4 generally describes a method to identify the optimal direction and optimal stimulation parameters with which to stimulate a bundle of white matter tracts in a patient's brain. The use of the term optimal stimulation parameters refers to parameters that may or may not be optimal however attempt to approach such a threshold. The application of the stimulation current may be performed using a stimulation apparatus such as the ones described herein or equivalent variants. The optimal direction is determined using a navigation module and the properties of the applied stimulation are determined using segmented preoperative imaging of the patient to identify tract functionality in combination with an informatics engine used to determine optimal stimulation parameters for the given tracts having that functionality.

Figure 30:
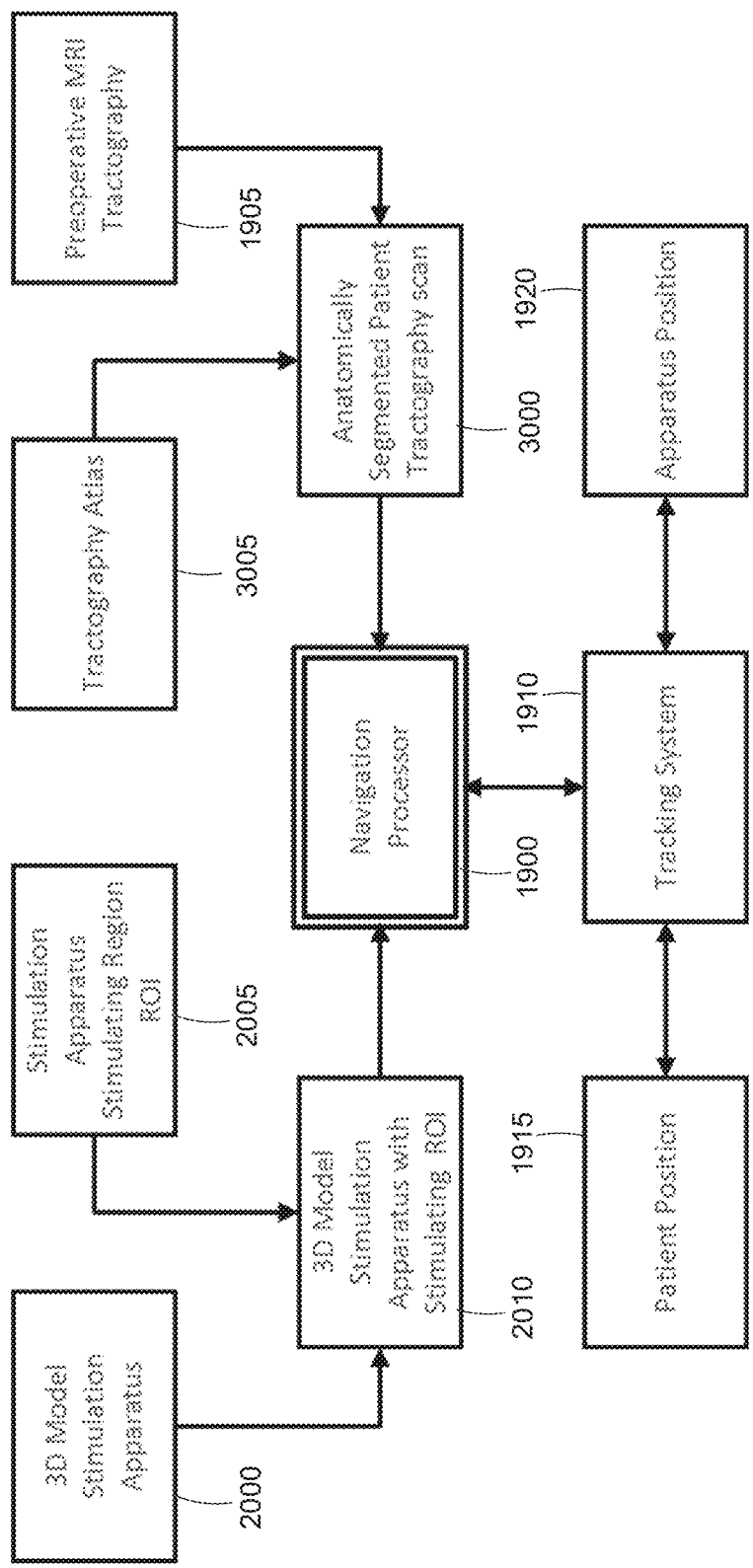
FIG. 30 Illustrates a block diagram showing exemplary inputs into a navigation system enhanced with inputs from an atlas segmentation and informatics engine.

FIG. 30 is a block diagram showing some exemplary navigation processor inputs to further clarify the execution of Procedure 4 as per the flow chart depicted in FIG. 18, using the stimulation system 2901, and will be described in further detail below.

Figure 32:
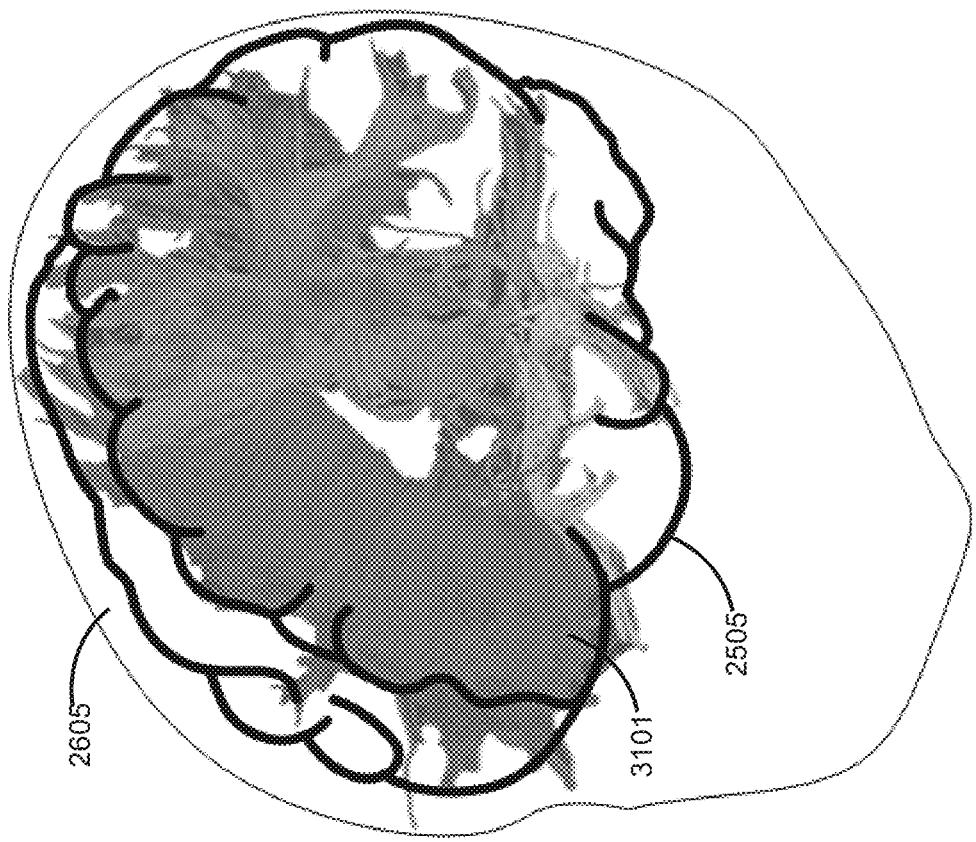
FIG. 32 Illustrates atlas segmented patient imaging within the head of the patient.

FIGS. 31 and 32 show exemplary segmented and culled preoperative Diffusion Tensor Imaging (DTI) derived tractography imaging of a patient's brain which may be input into the navigation processor 1900. FIG. 31 shows an exemplary portion of a patients preoperatively acquired tractography imaging 3101 segmented using the atlas segmentation engine 2905 to form an Anatomically Segmented Patient Tractography Scan 3000. The varying shades of darkness illustrate the independently segmented portions: the darkest fibers 3100, medium shade fibers 3110, and lightest fibers 3105 are representative of the patients Corpus collosum fiber tracts, their corticospinal white matter fiber tract and their Uncinate fasciculus white matter fiber tracts respectively. FIG. 32 shows these segmented tracts 3101 relative to a patient's skull 2605 and brain 2505.

For the informatics engine to determine optimal stimulation parameters applied through the stimulation terminals of a stimulation port apparatus, the stimulation terminals' positions relative to the patient's adjacent spatially registered segmented preoperative tractography scan, as well as the adjacent segmented tracts functions, must be known.

Figure 33:
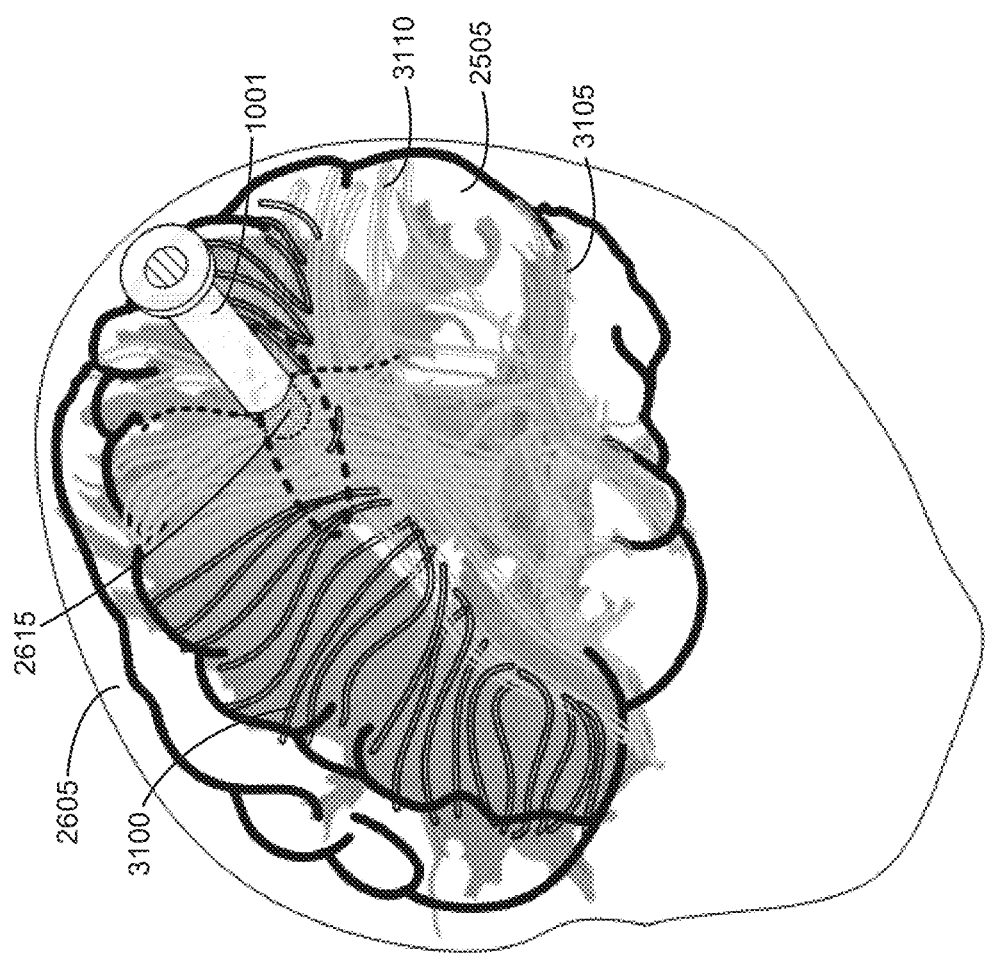
FIG. 33 Illustrates atlas segmented patient imaging within the head of the patient during a surgery, overlaid with a diagram of identical tractography for explanatory purposes.
Figure 34:
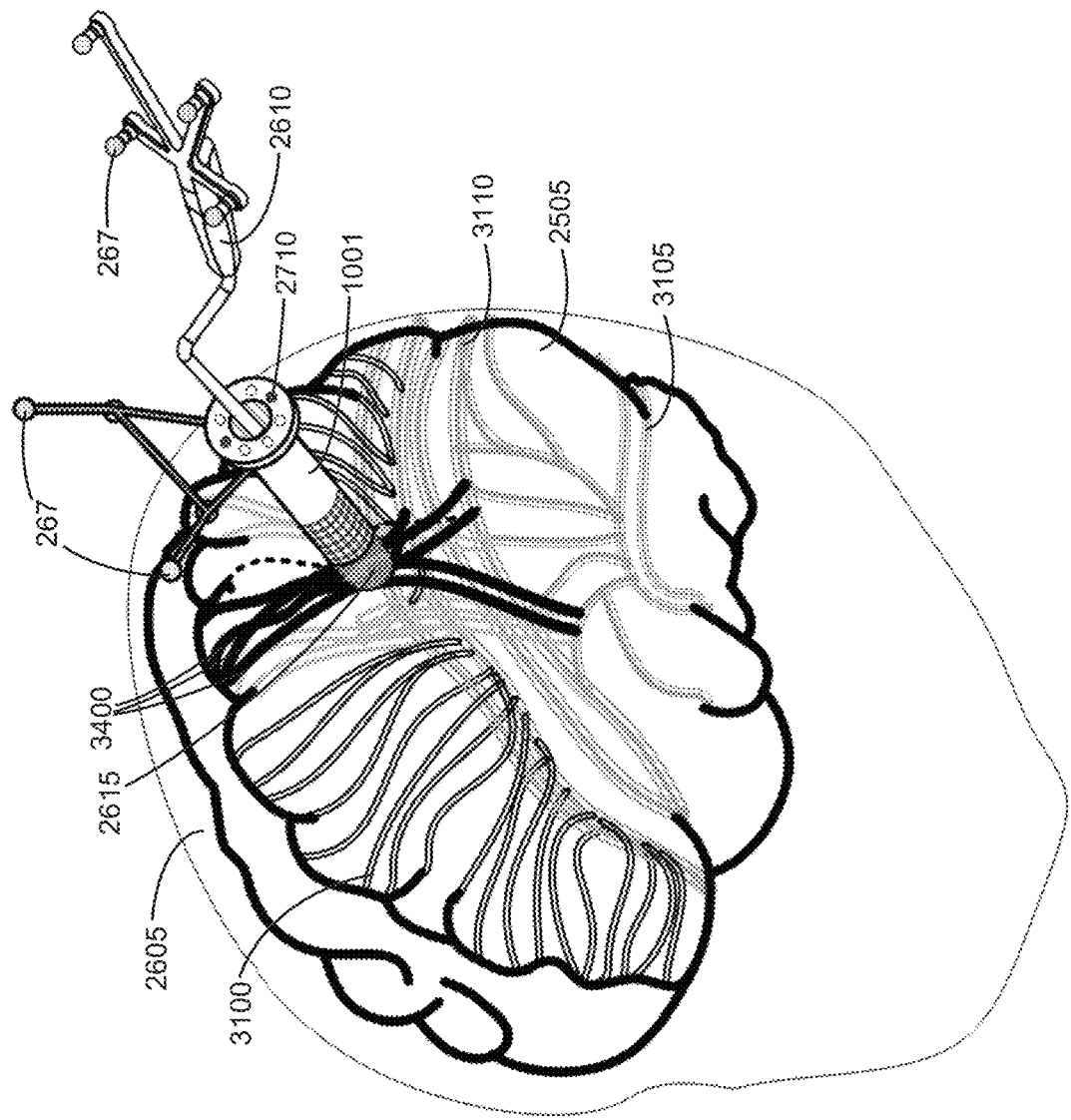
FIG. 34 Illustrates a diagram of tractography imaging within the head of the patient during a surgery.

An example is illustrated in FIGS. 33 and 34 where the patient's segmented tractography is shown relative to the patient's skull and stimulation apparatus 1001. FIG. 33 shows the patient's scanned tractography overlaid with equivalent graphical tractography having greater contrast and spatial distribution for illustrative purposes only, where the overlaid graphical tracts represent the exact same information as the scanned tracts only being more simply visualized for explanatory purposes as per the disclosure herein. FIG. 34 shows the segmented tractography diagram of FIG. 33 during a neurosurgical operation during which a stimulation procedure may be implemented such as per Procedure 4 in FIG. 18. The diagram in FIG. 34 is representative of potential information inputted into the Navigation System and Control and Processing Unit 1900 and the physical orientation of objects in the operating space. From this diagram it is apparent that the distal end of the stimulation ECoG port apparatus 1001 is positioned adjacently to white matter fiber tracts of the Corpus Collosum 3100. The ROI region 2615 of the apparatus shows the overlap of tracts and the volume in which a stimulation current may be applied by the tracked apparatus 1001. It is apparent that the highlighted tracts 3400 of the Corpus Collosum that may be stimulated overlap with ROI volume 2615 of the port 1001. Thus the Navigation System and Control and Processing Unit 1900 may determine the segments of these fiber tracts 2800 located in the volume and further analyze their directionality (relative to the orientation of the apparatus 1001) to determine an optimal stimulation current direction. The directionality of these tracts may be determined by processing the image data in the region 2615 relative to the orientation of the apparatus 1001 and applying known anatomical atlas information as outlined in publication "HUMAN BRAIN WHITE MATTER ATLAS: IDENTIFICATION AND ASSIGNMENT OF COMMON ANATOMICAL STRUCTURES IN SUPERFICIAL WHITE MATTER" (Neuroimage. 2008 Nov. 15; 43(3): 447-457). In addition, comparing the diagram in FIG. 34 to the diagram in FIG. 27, it should be apparent from the differences in tractography shades (for example between the Corpus Collosum and the Corticospinal tract) that in this diagram the potential information inputted into the Navigation System and Control and Processing Unit 1900 also includes the segmented tractography as described above. The segmented tractography may be used by the informatics engine for filtering and/or computing the optimal stimulation parameters for displaying to the surgeon as described in further detail below. Referring back to FIG. 30, in order to provide such information to the informatics engine 2900 via the Navigation System and Control and Processing Unit 1900, the Preoperative MRI Tractography 1905 must be integrated with the Tractography Atlas 3005 (by methods known in the art such as those provided by international application PCT/CA2014/000740, titled "SYSTEM AND METHOD FOR CONNECTIVITY MAPPING" which is incorporated by reference. MRI Tractography data 1905 and Tractography Atlas 3005 is used to form an Anatomically Segmented Patient Tractography Scan 3000 that may then be subsequently inputted into the Navigation System and Control and Processing Unit 1900.

The information provided above regarding the tracts located within the stimulation ROI (such as their function inferred from their segmented anatomy) may allow the informatics engine to acquire contextual information relative to the impending stimulation. In some embodiments the contextual information may provide the informatics engine with filters through which relevant stimulation information may be extracted from a database containing stimulation assisted neurosurgical data from previous surgeries. For example, the position of the stimulation apparatus relative to a patient's brain along with the anatomical function of the tracts to be stimulated may provide two filters through which relevant information may be extracted about previously employed stimulation parameters. An example of such data of a stimulation parameter may be the average amperage current used in previous stimulation applications to achieve a successful stimulation in similar anatomical positions on similar patients for tracts with the same anatomical function. Once this data is acquired it may be subsequently displayed to a surgeon. The surgeon informed with this additional information may then select stimulation parameters to better assist them in acquiring the desired stimulation response from the patient.

Procedure 4 as shown in the flow chart depicted in FIG. 18 reflects a similar process to that of any of Procedures 1 to 3 but in addition to employing the inputs provided by stimulation system 1901 it extends to employ the atlas segmentation 2905 and informatics 2900 engines as per the stimulation system 2901. This embodiment of the procedure shown in FIG. 18 may extend any of Procedures 1 to 3 as described above by providing optimal stimulation parameters to be used during the applied stimulation step 1816. In the embodiment shown of the stimulation system 2901 both the atlas segmentation 2905 and informatics 2900 engines are connected as per the Navigation System and Control and Processing Unit 1900. Procedure 4 extends on the steps performed in any of procedures 1 to 3 with four additional steps that may be executed to provide optimal stimulation parameters to be used during the application of the stimulation current to the patient. The first two steps of this addition extend before the initial step of any of Procedures 1 to 3, where in the first step 1800 a Tractography Atlas 3005 is registered with the Preoperative MRI Tractography 1905 of the patient and subsequently segmented by the atlas segmentation engine 2905 to form an Anatomically Segmented Patient Tractography Scan 3000. Once this scan is acquired the procedure advances to step 1804 of any of Procedures 1 to 3 and continues until step 1814, with the segmented tractography scan 3000 in place of the tractography component of the preoperative imaging 1905. Once Procedure 4 reaches step 1814, it proceeds to step 1828 instead of advancing to step 1816 as per any of Procedures 1 to 3. In step 1828 the informatics engine 2900 uses contextual information acquired by the stimulation system 2901 to produce optimal stimulation parameters for the impending stimulation application. After the optimal stimulation parameters are produced, the following step 1826 is to configure the stimulation apparatus for its initial stimulation, at which point Procedure 4 advances back into any of the Procedures 1 to 3. It should be noted that in some embodiments these parameters will be presented to the surgeon and may require a prompt from the surgeon to approve the configuration of the stimulation apparatus with the produced parameters. It should be apparent that such a prompt may constitute an additional step (not shown) between steps 1828 and 1826. In addition this prompting of the surgeon in some embodiments of the procedure described in FIG. 18 may be applicable to continue to the next step at any of the steps where it is deemed a requirement to ensure the safety of the patient and may act as a check to safeguard against potential systems errors in the application of the method described. It should also be noted that the loop 1816→1818→1820→1821→1824→1816 described above in Procedure 2 will now be formed as follows 1816→1818→1820→1821→1828→1826→1816. In this form of the loop, step 1824 is replaced by the steps 1828 and 1826. In this loop these two steps form an integral stage used to reconfigure the stimulation apparatus for every subsequent stimulation as per the optimal stimulation parameters produced by the informatics engine 2900 in step 1828. As is apparent from the description of Procedure 4, the addition of the four steps to any of the Procedures 1 to 3 may allow for the engagement of the informatics engine 2900 in determining optimal stimulation parameters for potentially providing better stimulation results.

Use of Probe with Navigation System, Tractography Segmentation, and Informatics Engine to Determine Correct Stimulation Pulse: Retrieving Stimulation Information and Ranking Based on Database To elucidate the functioning of the informatics engine within the context of stimulation assisted neurosurgical operations as disclosed herein, a flow chart describing an exemplary manner in which the informatics engine may produce optimal stimulation parameters is provided in FIG. 35. A summary of neuronal firing induced by electrical stimulation in the central nervous system is first provided to clarify the subsequent description of FIG. 35. Stimulating neurons is a method that has been employed for years in the field of neuroscience. Given the vast number of types of neurons and neural networks in the brain many biological attributes such as sub-threshold oscillations, chemical makeup, refractory periods, biological location and biological function influence the effectiveness of stimulation parameters in causing action potentials (nerve stimulation) to occur in such neurons and neural networks. It has been found that different functional areas of the brain will respond better to different variations in stimulation parameters such as current amperage, frequency, stimulation train design, phase difference, etc.

Optimization of stimulation parameters during cortical mapping or other surgical procedures involves minimizing trauma to brain tissue while still effectively stimulating the intended nerve bundle without causing an epileptic response. To accomplish such an optimal stimulation the parameters should minimize amperage to the lowest amount required to stimulate the nerve, as high amperages can cause epileptic responses in patients resulting in the invalidation of any functional response information gained during such an epileptic stimulation. In addition higher amperages can cause damage to the stimulated tissue by burning it, resulting in the formation of scar tissue and potentially severing the nerve bundle fibers. Generally it is difficult to estimate the lowest amperage needed to stimulate a nerve bundle as there is a high variation in the amount of amperage required to stimulate nerves of different types and in different functional areas of the brain. As described above and reiterated here, during some stimulation assisted neural procedures each suspected nerve bundle (or functional area of the brain) may be stimulated with a low amperage after which the patient is observed to detect a functional response. If no response is detected the stimulation amperage is increased at a chosen interval and the process is repeated until either a functional or epileptic response is detected. In some cases if an epileptic response is detected the amperage is lowered to a single interval below the level at which the epileptic response was detected (after the epileptic response has subsided in the patient) and the patient is stimulated again at this amperage (at the same nerve bundle) and observed again for a functional response. Given a functional response isn't detected this nerve bundle is recorded as non-responsive (with respect to the area corresponding to the patients functions that is suspected to be related). It is apparent that this method can be time consuming especially during such an invasive procedure when the patient's brain is exposed to the operating room environment.

Stimulation frequency (of the input electrical signal) is also a consideration when optimizing stimulation parameters as different neurons and neural networks vary in their response to input frequency of the electrical stimulation signal. The refractory period of neurons after stimulation dictates the time it takes for the neuron to return to a state (electrochemical) at which it may be stimulated again. Therefore choosing a stimulation frequency greater than this can result in inefficient stimulation of the selected nerve bundle, as not all of the neurons will be able fire on each cycle of stimulation. Choosing a frequency below this can guarantee that all neurons of the selected type can fire continuously and cyclically in coherence with the input electrical stimulation signal. The exploitation of this phenomenon may benefit a surgeon in cases where increasing amperage may approach a tissue damage threshold in a patient.

Epileptic responses in patients are correlated with the number of neurons being stimulated simultaneously. Where a larger number of neurons firing in a given time interval increases the probability of an epileptic seizure. Given the discussion above concerning higher frequency stimulation, it is apparent that selection of such a stimulation frequency (greater than the refractory period of the selected neurons) may reduce the number of neurons fired per cycle and the resulting likelihood of an impending epileptic response in some cases may be alleviated.

Sub-threshold oscillations of potentials in axons also play a role in dictating optimal stimulation input frequency. As the axon sub-threshold potential oscillates it periodically reduces and increases the potential gap between the potential of the axon and the threshold potential at which the neuron fires. Given that this biological phenomenon differs across varying neuron types, such as the interneuron or pyramidal neuron cells, an input stimulation frequency can be selected to minimize the required amperage to induce the neuron to fire thereby reducing any potential trauma to the patient's brain. This amperage would be the minimum (or near minimum) amperage required to cause the neuron to reach the threshold firing potential during a cycle of the axon's sub-threshold potential fluctuation.

Given the description above an exemplary method for the selection of optimized stimulation parameters is provided as follows. A database information system such as the informatics system disclosed in international patent publication WO2014/139021, herein incorporated by reference, may be employed during a stimulation assisted neurosurgical operation to collect data and compute collected data to provide a user with optimal stimulation parameters in a context specific manner. In such a case the electrical stimulation input parameters used during the surgery may be recorded along with parameters related to the operation being performed such as the location of the stimulation device in the patient (functional area, type of neurons being stimulated, etc.), pathology, attributes of the patient (male or female, verbal IQ score, etc.), registered location with respect to an atlas segmented imaging of the patient, characterization data acquired during the operation (Raman spectrum, polarization sensitive optical coherence tomography (PSOCT) scan, intraoperative MRI), registered preoperative data, functional response of patient to specific stimulation, and other data that may be recorded and which may influence the electrical stimulation parameters employed during such a functional stimulation operation. Once acquired this data may be used to calculate the most probabilistically effective electrical stimulation parameters during the execution of the stimulation assisted neurosurgery.

Figure 35:
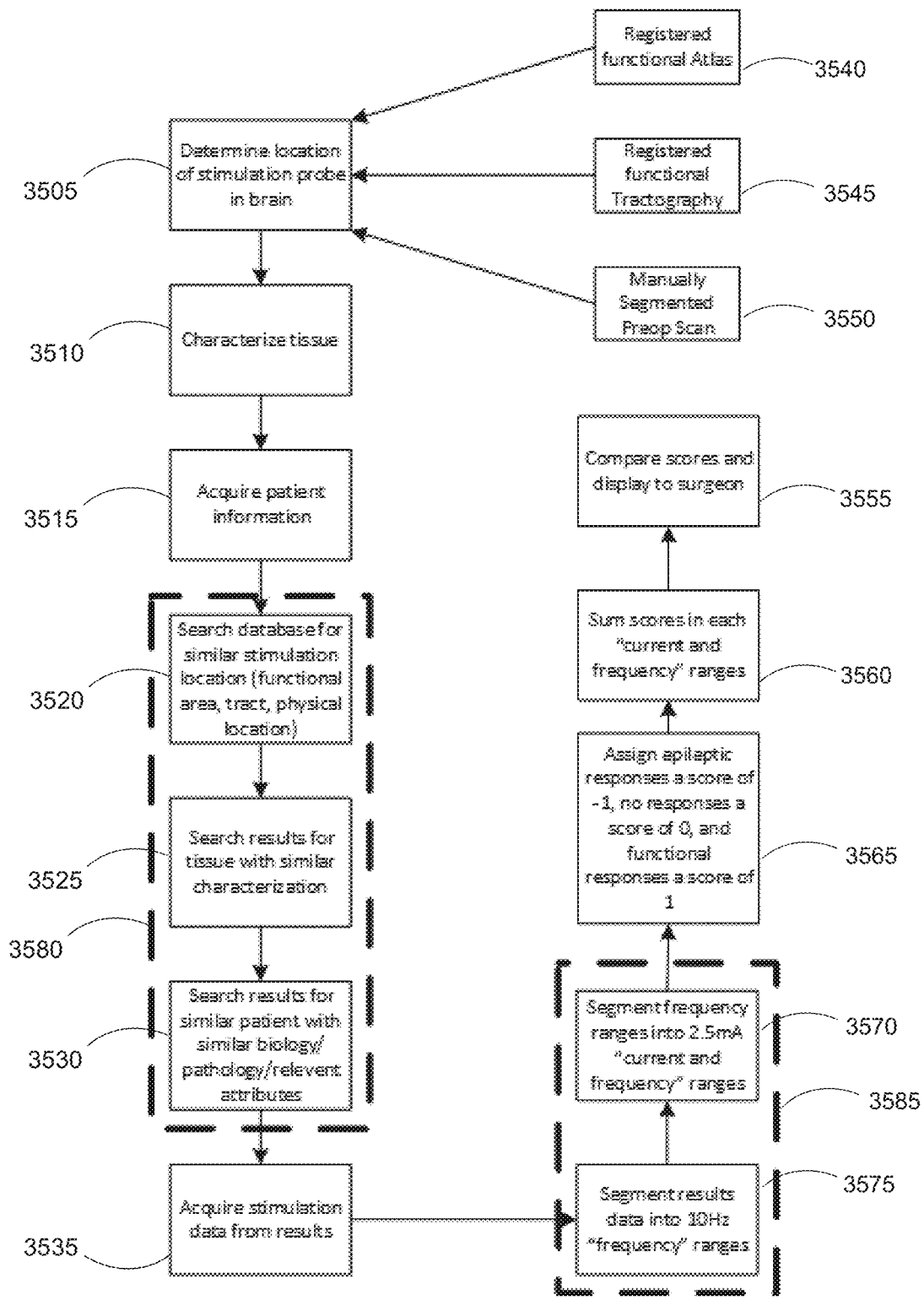
FIG. 35 Illustrates a flow chart describing the determination of applicable stimulation pulse parameters.

The flow chart in FIG. 35 describing an exemplary method to calculate such parameters will be described in further detail as follows. The initial step 3505 in the flow chart is to utilize the navigation system and various locatable registered patient imaging to determine the location of the stimulation apparatus with respect to the patient's anatomy, such as their white matter brain tracts. The inputs 3540, 3545, and 3550 into this step may provide further information about the area being stimulated to the navigation system. For example, as described in further detail above, a registered functional tractography atlas 3545 may provide information as to the tract being stimulated and its corresponding function. In addition a registered functional atlas 3540 may provide information of the functional area in the brain in which the stimulation is being applied and its corresponding functions. Lastly a manually segmented (for example with input from the surgeon) preoperative patient scan 3550 may be used to validate a surgeons own perception of the anatomical segmentation of the patient's imaging against the automatically segmented version.

After acquiring the navigation data related to the location of the stimulation apparatus the brain tissue adjacent the apparatus may be characterized 3510 using a multitude of intraoperative characterization methods such as fluorescence imaging, Raman spectroscopy, and other methods of tissue characterization made available by gaining surgical access to the tissue to be stimulated. Next the system may be inputted with or acquire relevant patient specific information 3515 that may be used for determining optimization parameters for electrical stimulation. For example, a patient's age, gender, IQ, and other various factors that may or may not assist the informatics system in producing the optimal stimulation parameters. The next section in the method 3580 is to perform a database search of the informatics system to filter it for relevant context specific electrical stimulation parameters the apparatus may be configured with. It should be noted that this search and more specifically the filters applied are provided for exemplary purposes only and other search sequences and/or filters may be used as they pertain to finding optimal electrical stimulation parameters which may be applied during the relevant procedure. The first filter 3520 in the exemplary search sequence extracts only stimulation parameters which were employed in similar anatomical locations to the one where the stimulation will be applied within the patient. Examples of such locations could be the motor cortex, the language cortex, the right superior frontal lobe, or any other anatomical location relevant to the surgery being performed. The second filter 3525 in the exemplary search sequence extracts only stimulation parameters used on tissues with similar characterization metrics to the tissue within the patient that is to be stimulated. Examples of such characterization metrics can be the tissues Raman spectrum, fluorescence spectrum, and chemical composition. The third filter 3530 in the exemplary search extracts only stimulation parameters used on patients with similar relevant attributes to the patient being operated on. Examples of such attribute include the patient's pathology, their sex, and their verbal IQ. After the filters are applied the extracted stimulation parameters are acquired from the database 3535 by the informatics system.

The following section in the method 3585 performs a segmentation of the results so they may be categorized in a logical manner and provided to the surgeon to be assessed. For exemplary purposes it will be assumed that the extracted stimulation parameters were formed with only two variables, being the stimulation current and stimulation frequency. However, multiple variables may be used in addition or substitution to the ones mentioned including but not limited to phase shift and frequency train. The first step 3575 in this section is to segment the acquired data into 10 Hz frequency ranges. The above mentioned search sequences are customizable and if different stimulation parameters are available in the data they should be segmented accordingly. For example if the previous data was inclusive of variable frequency trains used in electrical stimulation as opposed to constant frequencies, the data may be segmented accordingly, such as a 10 Hz-5 Hz over 5 s variable frequency train data could be segregated from a 10 Hz-3 Hz over 4 s variable frequency train data. The segmentations should be chosen in ranges to maximize the utility of the data. The next step 3570 is to further segment the ranges from the previous step into 2.5 mA ranges.

Once the data is segmented into sections defined by amperage and frequency of the electrical stimulation input, each datum in each section may be assigned a weighted number to quantify the effectiveness of that stimulation pattern in attaining the desired result from the patient to which that parameter was applied. In the exemplary method depicted in FIG. 35 the desired result is a functional response of the patient, where no functional response implies the location of the stimulation may or may not be related to the function of interest and an epileptic response is least desired. Therefore to quantify these results in order to provide useable information to the surgeon 3565, scores can be assigned such as: the desired result (an observed functional response) a 1, a neutral result (no observed response) a 0, and an undesirable response (an epileptic response) a −1. After weighting each response of a previous patient to its corresponding stimulation parameter, the weights of the individual datum in each section may be summed 3560. The results may be provided to the surgeon 3555 (for example via a display 111), such as through a surface plot having two independent axis of amperage and frequency and a dependent axis of score, where the score corresponds to the sum of all of the weighted results in each segmented range.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. An apparatus for intraoperative tissue stimulation, comprising:
an access port having a hollow cylindrical body configured to receive at least one tool, a distal end configured to insert into a tissue, and a proximal end configured to substantially remain at a surface of the tissue; and
at least one pair of electrical terminals coupled with the access port and configured to stimulate the tissue, wherein the at least one pair of electrical terminals is arranged as one of:
a diametrically opposing arrangement, each pair of electrical terminals of the at least one pair of electrical terminals configured to switch polarity between a positive polarity and a negative polarity and arranged longitudinally within the access port;
an adjacent arrangement, each pair of electrical terminals of the at least one pair of electrical terminals comprising an anode and a cathode, and each pair of electrical terminals of the at least one pair of electrical terminals diametrically opposing another pair of electrical terminals of the at least one pair of electrical terminals; and
a plurality of stimulation prongs located on a distal end of the electrical terminals;
a plurality of springs, each spring configured to couple to a stimulation prong;
a plurality of tracking markers placed on the proximal end of the port configured for tracking of the port with a surgical navigation system;
wherein the pair of electrical terminals produce a linear electrical potential across the two active terminals of opposite polarity;
wherein each stimulation prong and spring combination are configured to be collapsible, allowing each stimulation prong to deform on an uneven tissue surface.

2. The apparatus of claim 1, further comprising an electrical system coupled with the at least one pair of electrical terminals, wherein the at least one pair of electrical terminals is disposed in the access port at a circumference portion.

3. The apparatus of claim 1, further comprising an electrical system coupled with the at least one pair of electrical terminals, wherein the at least one pair of electrical terminals is disposed in the distal end of the access port at a circumference portion.

4. The apparatus of claim 1, further comprising a monopolar probe configured to insert through the hollow cylindrical body of the access port.

5. The apparatus of claim 1, further comprising at least one light emitting diode (LED) in the proximal end of the access port, the at least one LED configured to indicate activity of each pair of electrical terminals of the at least one pair of electrical terminals.

6. The apparatus of claim 1, further comprising:
a stimulation terminal controller coupled with the electrical terminals;
a controller and a processor coupled with the stimulation terminal controller;
a display coupled with the controller and the processor; and
a power source coupled with the controller and the processor.

7. An apparatus for intraoperative tissue stimulation comprising:
an access port having a hollow cylindrical body configured to receive at least one tool, a distal end configured to insert into a tissue, and a proximal end configured to substantially remain at a surface of the tissue;
at least one electrocorticography (EcoG) sensor coupled with the access port;
a plurality of stimulation prongs located on a distal end of the electrical terminals that are coupled to the access port;
a plurality of springs, each spring configured to couple to a stimulation prong;
a plurality of tracking markers placed on the proximal end of the port configured for tracking of the port with a surgical navigation system;
wherein at least one pair of electrical terminals are coupled to the access port and produce a linear electrical potential across two active terminals of opposite polarity;
wherein each stimulation prong and spring combination are configured to be collapsible, allowing each stimulation prong to deform on an uneven tissue surface.

8. The apparatus of claim 7, wherein the at least one pair of electrical terminals is arranged as one of:
a diametrically opposing arrangement, each pair of electrical terminals of the at least one pair of electrical terminals configured to switch polarity between a positive polarity and a negative polarity; and
an adjacent arrangement, each pair of electrical terminals of the at least one pair of electrical terminals comprising an anode and a cathode, and each pair of electrical terminals of the at least one pair of electrical terminals diametrically opposing another pair of electrical terminals of the at least one pair of electrical terminals.

9. The apparatus of claim 8, further comprising at least one light emitting diode (LED) in the proximal end of the access port, the at least one LED configured to indicate activity of each pair of electrical terminals of the at least one pair of electrical terminals.

10. The apparatus of claim 8, further comprising:
a detector terminal controller coupled with the at least one EcoG sensor;
a stimulation terminal controller coupled with the at least one pair of electrical terminals;
a controller and a processor coupled with the detector terminal controller and the stimulation terminal controller;
a display coupled with the controller and the processor; and
a power source coupled with the controller and the processor.

11. The apparatus of claim 10, further comprising at least one of:
a surgical navigation system coupled with a controller and the processor;
an imaging data module coupled with the controller and the processor;
an informatics engine coupled with the controller and the processor;
an image data segmentation module coupled with the controller and the processor;
an automated alignment system coupled with the controller and the processor; and a tracking system, coupled with the controller and the processor, for tracking surgical instruments.

12. The apparatus of claim 7, further comprising:
a stimulation terminal controller coupled with the at least one EcoG sensor;
a controller and a processor coupled with the stimulation terminal controller;
a display coupled with the controller and the processor; and
a power source coupled with the controller and the processor.

13. A method of intraoperatively stimulating tissue by way of an apparatus, comprising:
providing the apparatus, comprising:
providing an access port having a hollow cylindrical body configured to receive at least one tool, a distal end configured to insert into a tissue, and a proximal end configured to substantially remain at a surface of the tissue; and
providing at least one pair of electrical terminals coupled with the access port and configured to stimulate the tissue, wherein providing the at least one pair of electrical terminals comprises arranging the at least one pair of electrical terminals as one of:
a diametrically opposing arrangement, each pair of electrical terminals of the at least one pair of electrical terminals configured to switch polarity between a positive polarity and a negative polarity; and
an adjacent arrangement, each pair of electrical terminals of the at least one pair of electrical terminals comprising an anode and a cathode, and each pair of electrical terminals of the at least one pair of electrical terminals diametrically opposing another pair of electrical terminals of the at least one pair of electrical terminals;
providing a plurality of stimulation prongs located on a distal end of the electrical terminals;
a plurality of springs, each spring configured to couple to a stimulation prong;
inserting the access port into the tissue; and
applying an electrical potential to the tissue by activating the apparatus;
wherein the port further comprises a plurality of tracking markers placed on the proximal end of the port, the tracking markers configured for tracking of the port with a surgical navigation system;
wherein each stimulation prong and spring combination are configured to be collapsible, allowing each stimulation prong to deform on an uneven tissue surface.

14. The method of claim 13, wherein inserting the access port comprises inserting the access port into brain tissue.

15. The method of claim 13, wherein applying the electrical potential comprises configuring the electrical potential in relation to at least one parameter of frequency, amperage, voltage, and waveform.

16. The method of claim 13, wherein inserting an access port into the tissue comprises using preoperative imaging to navigate the access port.

17. The method of claim 13, wherein applying the electrical potential comprises directing the electrical potential from one pair of electrical terminals of the at least one pair of electrical terminals to another pair of electrical terminals of the at least one pair of electrical terminals.

18. The method of claim 13, wherein applying the electrical potential comprises directing the electrical potential from a monopolar probe inserted through the access port to the at least one pair of electrical terminals.

* * * * *